United States Patent [19]

Yamamoto et al.

[11] Patent Number: 4,539,148

[45] Date of Patent: Sep. 3, 1985

[54] PRODUCTION OF 1-OXACEPHAMS AND INTERMEDIATES

[75] Inventors: Sadao Yamamoto, Hyogo; Hikaru Itani, Osaka; Hiromi Takahashi, Hyogo; Teruji Tsuji, Osaka; Wataru Nagata, Hyogo, all of Japan

[73] Assignee: Shionogi & Co., Ltd., Osaka, Japan

[21] Appl. No.: 523,414

[22] Filed: Aug. 16, 1983

[30] Foreign Application Priority Data

Aug. 24, 1982 [JP] Japan ............................ 57-147268

[51] Int. Cl.$^3$ ................. C07D 205/08; C07D 487/04; C07D 309/12; C07D 403/12

[52] U.S. Cl. .............................. 260/239 A; 260/245.4; 544/90; 560/168; 560/170; 560/174; 560/183; 549/419; 549/420

[58] Field of Search ................................... 260/239 A

[56] References Cited

PUBLICATIONS

Shibahara et al., Chem. Abs. 99, 139636z, (1983).

*Primary Examiner*—Mark L. Berch
*Attorney, Agent, or Firm*—Wenderoth, Lind & Ponack

[57] ABSTRACT

Useful intermediates, 7α-acylamino-3-(oxo or exomethylene)-1-dethia-1-oxacepham-4α-carboxylates, are produced by the intramolecular carbenoid insertion of a 2-diazo-3-(oxo or exomethylene)-4-(3α-acylamino-2-oxoazetidin-4β-yl)oxybutyrate prepared in several steps from the corresponding oxazolinoazetidinone and diketone.

3 Claims, No Drawings

PRODUCTION OF 1-OXACEPHAMS AND INTERMEDIATES

This invention relates to a novel intermediate for producing 1-oxacephams, i.e. a 4-oxygenated butyric acid derivative represented by the following formula $$Y^1CH_2\underset{X}{\overset{\|}{C}}-R^2-COOR \tag{I}$$

wherein

R is an ester forming group;

$R^2$ is methylene, hydroxyiminomethylene, protected hydroxyiminomethylene or diazomethylene;

X is oxo or methylene; and $Y^1$ is hydroxy, protected hydroxy or a group represented by the following formula

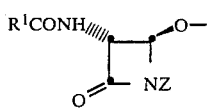

in which $R^1$ is optionally substituted alkyl, aralkyl or aryl and Z is hydrogen or a N-protecting group.

The compound (I) can be used in a manner as described below, i.e., the compound (I) is converted, if required, into one of the 4-oxygenated butyrates represented by the following formula

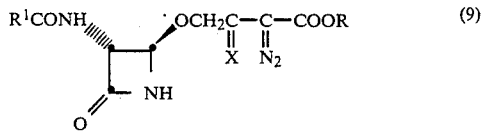

wherein R, $R^1$ and X are as defined above, and the latter is subjected to the so-called intramolecular carbenoid insertion to afford a 7α-acylamino-3-(oxo or exomethylene)-1-dethia-1-oxacepham-4α-carboxylate represented by the following formula

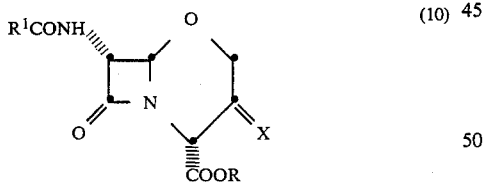

wherein R, $R^1$, and X are as defined above, known by, e.g., Japanese Patent Application Kokai Nos. 53-21188, 53-101391, and useful as an intermediate for preparing various 1-oxacephem antibacterials known by, e.g., Japanese Patent Application Kokai Nos. 49-133594, 52-65393, Tetrahedron Letters, 1978, [5], 409, etc.

In the above formula, R is an ester forming group or equivalent carboxy protecting group in the field of cephalosporin and penicillin chemistry and capable of being introduced or deprotected under a condition showing no adverse effect on other part of the molecule. Representatives of them are $C_1$ to $C_5$ aliphatic ester, e.g., methyl, ethyl, propyl, t-butyl, trichloroethyl, allyl or the like; $C_7$ to $C_{15}$ aralkyl ester, e.g., benzyl, methylbenzyl, dimethyl benzyl, methoxybenzyl, ethoxybenzyl, nitrobenzyl, aminobenzyl, diphenylmethyl, phthalidyl, phenacyl or the like; mono or dicyclic $C_6$ to $C_{12}$ aryl ester, e.g., phenyl, pentachlorophenyl, indanyl or the like; and an ester with $C_1$ to $C_{10}$ N-hydroxyamino compound, e.g., acetone oxime, acetophenone oxime, acetoaldoxime, N-hydroxysuccinimide, N-hydroxyphthalimide and the like. A reactive amide and anhydride with a carbonic or carboxylic acid are equivalent analogous protective groups.

The protective group is usually eliminated in the target compound. So, the structure is unimportant as far as the carboxy is protected during the reaction. Other representative carboxy-protecting groups are described in, e.g., McOmie, "Protective groups in Organic Chemistry", Plenum Press, London (1973), Flynn Ed., "Cephalosporins and Penicillins", Academic Press, N.Y., (1972), etc.

Representative $R^1$ is $C_1$ to $C_{10}$ optionally substituted alkyl, aralkyl or aryl, e.g., methyl, phenoxymethyl, benzyl, phenyl, methylphenyl, dimethylphenyl, cyanophenyl, nitrophenyl, methoxyphenyl, chlorophenyl, etc.

Representative Z include $C_1$ to $C_5$ alkanoyl and tri-$C_1$ to $C_5$-alkylsilyl.

Representative protective group for $R^2$ is tri-$C_1$ to $C_5$-alkylsilyl or optionally cyclic 1-$C_1$ to $C_5$-alkoxy-$C_1$ to $C_5$-alkyl, e.g., trimethylsilyl, dimethyl-t-butylsilyl, methoxymethyl, tetrahydrofuranyl, tetrahydropyranyl, etc.

The $R^1CO$ group is replaceable by any other acyl at any desired stage in the course from the product of this invention to the target oxacephem having antibacterially suitable acyl. Thus, $R^1$ is usually chosen from that only suitable for the reactions of this invention and its structure is widely variable.

The compounds of this invention is produced and used by the method as illustrated below:

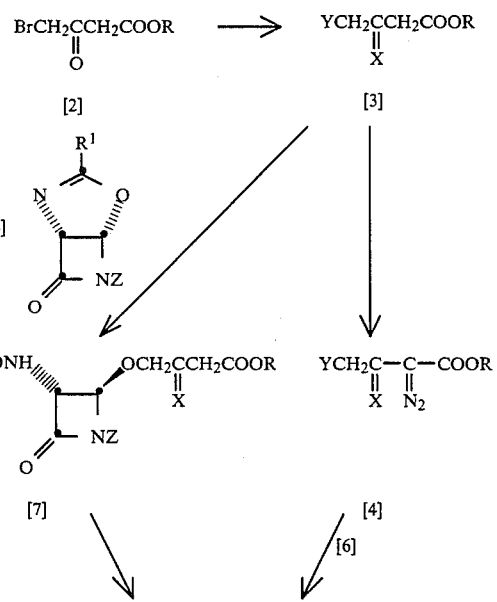

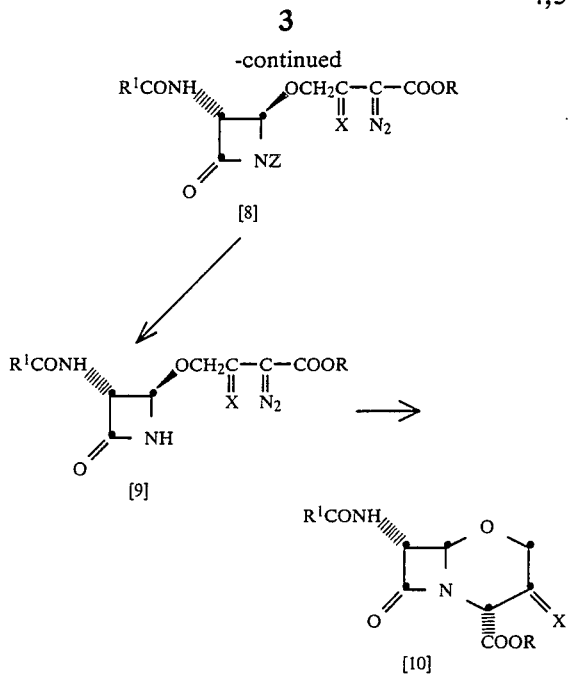

in which Y is hydroxy or protected hydroxy.

For example, diketone (1) is treated with bromine and water to give 4-bromoacetoacetic acid (2'). This (2') is esterified conventionally to give a 4-bromoacetoacetate (2). Replacing water with an alcohol in the reaction as above, diketone (1) gives the corresponding 4-bromoacetoacetate ester (2) directly. The 4-bromoacetoacetate (2) is conventionally hydrolyzed with aqueous base, e.g., alkali metal formate, at 30° to 90° C. to give hydroxyacetoacetate (3). This (3) is treated with a diazotizing reagent, e.g., methanesulfonyl azide, benzenesulfonyl azide, p-toluenesulfonyl azide or p-carboxybenzenesulfonyl azide, for 1 to 50 hours at 0° to 25° C. affording a diazoalcohol (4) in which X is oxo.

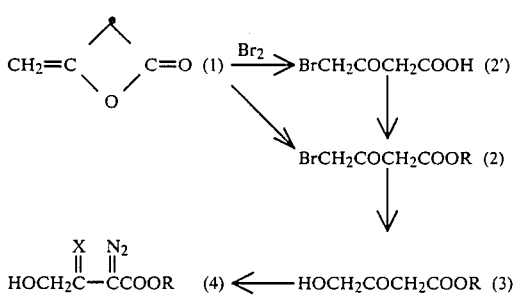

Alternatively, an acetoacetate (4-I) is treated with a nitrite or nitrogen oxide at 0° to 50° C. to give a 2-hydroxyiminoacetoacetate (4-II). This (4-II) is conventionally O-protected, e.g. with trialkylsilyl chloride, at 0° to 50° C. to give an enolsilyl compound (4-III). The latter is oxidized, e.g., with a percarboxylic acid, at 0° to 60° C. to give a disilyloxyketone (4-IV) as a mixture of syn-anti isomers. This (4-IV) is subjected to the Witting reaction or Horner-Emmons reaction for introducing methylene to give a methylenedisilyloxyketone (4-V) as a mixture of syn-anti isomers. The latter (4-V) is deprotected to give an oxime (4-VI) and treated at 0° to 80° C. with an aminating reagent, e.g. chloramine, dinitrophenoxyamine, benzenesulfonyloxyamine, trimethylphenylsulfonyloxyamine, O-(diphenylphosphinyl)-hydroxylamine or the like, to give a diazoester (4) wherein $Y^1$ is hydroxy and X is methylene.

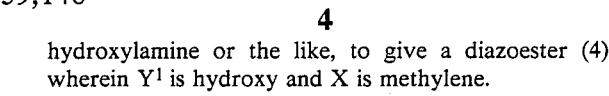
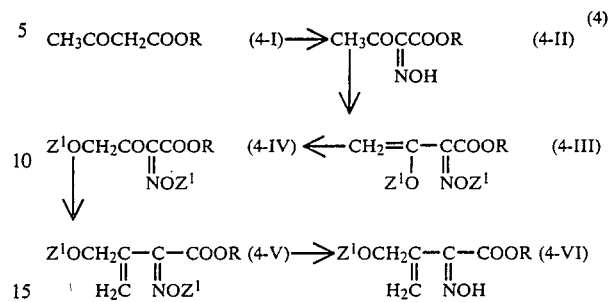

wherein $Z^1$ is a hydroxy-protecting group.

An oxazolinoazetidinone (6) is condensed with this (4) in the presence of an acid, e.g., antimonium chloride, boron trifluoride, tin chloride, titannium chloride, zinc chloride of the like Lewis acid, to give the corresponding azetidinyloxyazobutyrate (8) or an oxazolinoazetidinone (6) is treated with a hydroxyacetoacetate (3) affording an azetidinyloxyacetoacetate (7), and the latter is treated with a diazotizing reagent, e.g., an alkylsulfonyl azide or arylsulfonyl azide as exemplified above, to afford an azetidinyloxyazobutyrate (8).

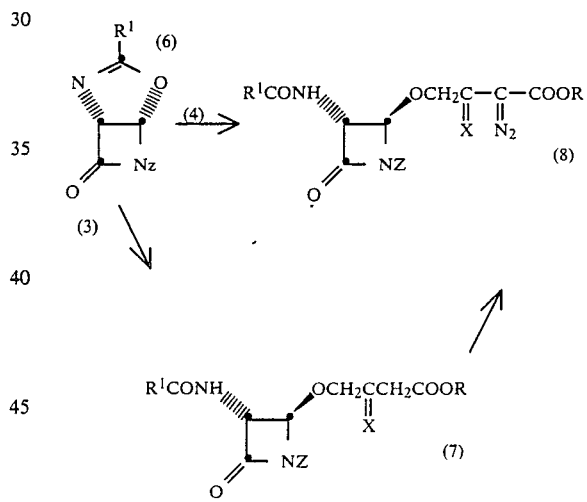

Further, the azetidinyloxyazobutyrate (8) wherein X is methylene is prepared from a 4-hydroxyacetoacetate (3) by nitrosylating to an oxime (8-I), O-protecting to a protected oxime (8-II), subjecting Wittig reaction to an exomethylene (8-III), deprotecting to a hydroxyoxime (8-IV), condensing with an oxazolinoazetidinone (6) to an azetidinobutyrate (8-V), and aminating.

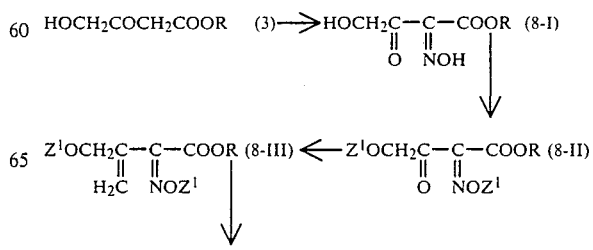

-continued

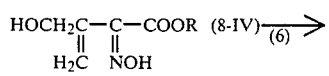

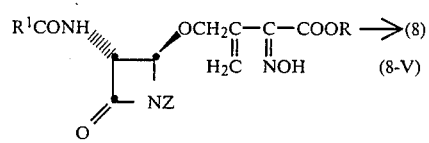

If Z is not hydrogen, this azetidinyloxyazobutyrate (8) is conventionally N-deprotected to give the N-unsubstituted azetidinone (9). The latter is subjected to the carbenoid insertion, e.g., with copper powder, copper bisacetylacetonate, copper sulfate, dirhodium tetraacetate or palladium triacetate, in a solvent, e.g., benzene, toluene, or tetrahydrofuran, at 50° to 110° C. for 1 to 6 hours (J. Am. Chem. Soc., 102, 6161 (1980); Japanese Patent Application Kokai No. 55-27169) or by irradiating with a tangusten lamp or mercuric lamp at 40° to 80° C. to afford a 1-oxacepham (10).

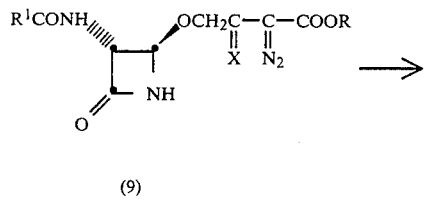

(9)

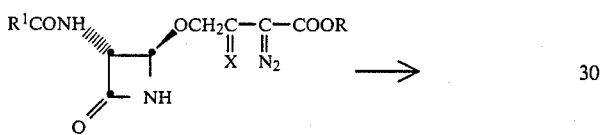

(10)

The novel processes of this invention is summarized as follows, in which symbols are as defined before, unless otherwise specified:

(1) an oxazolinoazetidinone (6) is treated with 4-hydroxybutyrate (I, $Y^1$=hydroxy) in the presence of acid (especially Lewis acid) to afford a 4-(optionally 1-protected-3α-acylamino-2-oxoazetidin-4β-yl)oxybutyrate [I, $Y^1$=optionally 1-protected 3α-acylamino-2-oxoazetidin-4β-yl)oxy], e.g., for 1 to 10 hours at 10° to 110° C. in a non-polar solvent.

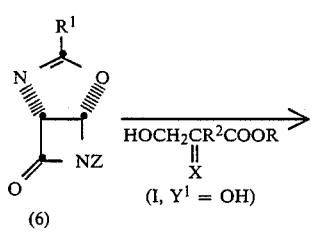

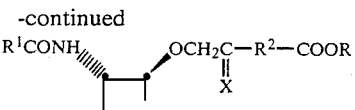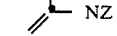

(8)

(2) a 4-(3-acylamino-2-oxoazetidin-4-yl)oxy-2-azobutyrate (9) is subjected to the carbenoid insertion or photo-reaction to afford 7α-acylamino-3-X-1-dethia-1-oxacepham-4α-carboxylate (10), e.g., for 30 minutes to 5 hours at 50° to 100° C. in a nonpolar solvent.

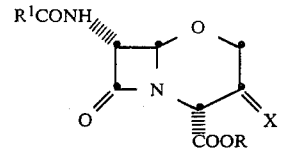

(9)

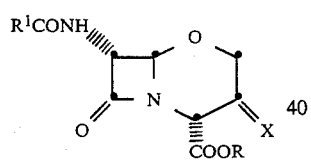

(10)

(3) a 4-$Y^1$-substituted-acetoacetate (I, X=oxo, $R^2$=methylene) is treated with a diazotizing reagent as specified above to afford a 2-diazo-4-$Y^1$ substituted-acetoacetate (I, X=oxo, $R^2$=diazomethylene) e.g., for 1 to 10 hours at 0° to 80° C. in a polar non-aqueous solvent.

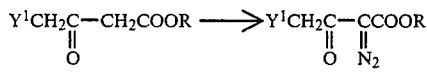

(4) a 4-$Y^1$-substituted-acetoacetate (I, $R^2$=methylene) is treated with a nitrosylating reagent (e.g. nitrite, $NO_2$) giving corresponding 2-hydroxyimino-4-$Y^1$ substituted-acetoacetate (I, $R^2$=hydroxyiminomethylene), e.g., for 1 to 10 hours at −10° to 80° C. in an aqueous solvent.

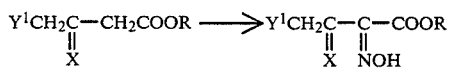

(5) a 4-$Y^1$-substituted-2-hydroxyimino-3-X-substituted butyrate (I, $R^2$=hydroxyiminomethylene) is treated with an aminating reagent to give the corresponding 4-$Y^1$-substituted-2-diazo-3-X-substituted butyrate (I, $R^2$=diazomethylene), e.g., for 1 to 10 hours at −30° to 70° C. in a non-polar solvent.

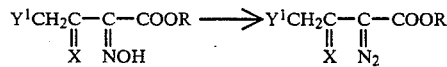

(6) a 4-Y¹-substituted-acetoacetate (I, X=oxo) is subjected to the Wittig reaction for introducing methylene to afford the corresponding 3-Y¹-substituted-methyl-3-butenoate (I, X=methylene), e.g., at −10° to 60° C. for 1 to 10 hours in a non-polar solvent.

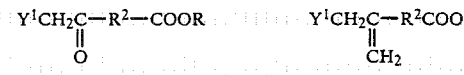

The reaction referred to above are usually done at a temperature between −30° C. and 100° C., especially −20° C. and 50° C. for a time between 10 minutes and 10 hours in a solvent, if required under anhydrous condition, according to a conventional method, e.g., anhydrous or inert gas protection of the reaction medium, stirring, etc. The solvent for the reaction may be an industrial solvent belonging to the hydrocarbon (e.g. pentane, hexane, octane, benzene, toluene, xylene), halohydrocarbon (dichloromethane, chloroform, carbon tetrachloride, dichloroethane, trichloroethane, chlorobenzene), ether (e.g. diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), sulfoxide (e.g., dimethyl sulfoxide, thiane-1,1-dioxide), carboxylic acid (e.g., formic acid, acetic acid, propionic acid), organic base (e.g., diethylamine, triethylamine, pyridine, picoline, collidine, lutidine, quinoline), alcohol (e.g., methanol, ethanol, propanol, hexanol, octanol, benzyl alcohol), water, sulfur dioxide or the like or a mixture of more than two of above industrial solvents, when appropriate for the reaction to be used.

The product of above reactions can be isolated by removing unreacted starting materials, by-products, solvents or the like by extraction, evaporation, washing, concentration, precipitation, filtration, drying or the like conventional method and then purified by e.g., adsorption, elution, distillation, precipitation, separating out, chromatography or the like conventional work up procedure.

Following examples illustrate the embodiments of this invention.

Experimental work up is usually carried out by treating the reaction mixture, if required after diluting with water, dichloromethane or the like, washing with water, drying, concentrating under reduced pressure and/or purifying the resultant material, if required after silica gel chromatographic purification, by crystallization, precipitation, filtration or the like.

Abbreviations used in the Examples are explained below:
Et=C₂H₅
Ph=phenyl
THF=tetrahydropyran-2-yl
—=t-butyl This invention is further explained by illustrating the following Preparations and Examples.

PREPARATION 1

Production of the starting material, 4-bromo-3-ketobutyric acid ethyl ester (2a).

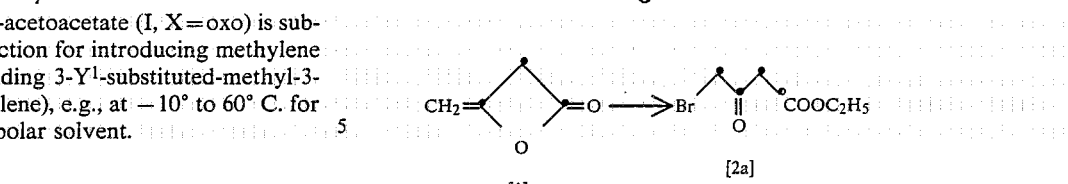

To a solution of diketone (1) (80 ml, 1.035 mole) in anhydrous dichloromethane (200 ml) is added dropwise a solution of bromine (56.5 ml, 1.035 moles) in anhydrous dichloromethane (100 ml) during 30 minutes at −40° C. with stirring. To this mixture is then added dry ethanol (82 ml, 1.40 moles) dropwise at −20° C. to −30° C., and the mixture is stirred at room temperature for 2 hours after the end of the addition. The reaction mixture is concentrated to remove the solvent, and then the residual solution is distilled under reduced pressure to give the title compound (184 g, Yield: 85%).

b.p.⁴: 94°–96° C.

IR (CHCl₃): 1740, 1726 cm⁻¹.

NMR (EM-390, CDCl₃, δ): 1.27 (3H, t, J=7.5 Hz, —CH₂C$\underline{H}$₃), 3.69 (2H, s, —C$\underline{H}$₂COOC₂H₅), 4.07 (2H, s, —C$\underline{H}$₂Br), 4.20 (2H, q, J=7.5 Hz, —C$\underline{H}$₂CH₃).

PREPARATION 2

Production of the starting material, 4-bromo-3-ketobutyric acid diphenylmethyl ester (2b).

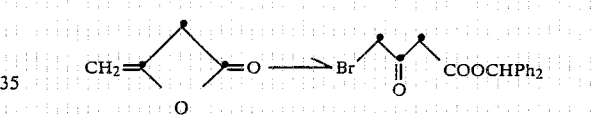

To a solution of diketone (1) (43.5 g, 0.518 moles) in dry dichloromethane (200 ml) is added dropwise a solution of bromine (82.7 g, 0.518 moles) in anhydrous dichloromethane (100 ml) at −40° C. to −30° C. over a 30 minutes period. To this mixture is then added a solution of benzhydrol (105.0 g, 0.568 moles) in anhydrous dichloromethane (100 ml) at −20° C. to −30° C., and stirred at room temperature for 1 to 1.5 hours after the end of the addition. The reaction mixture is concentrated under reduced pressure, and the residue is purified by silica gel column chromatography to give the title compound (98.9 g, Yield: 55%).

IR (CHCl₃): 1732, 1662, 1626 cm⁻¹.

NMR (T-60, CDCl₃, δ): 3.70 (2H, s, —C$\underline{H}$₂COOCHPh₂), 3.89 (2H, s, —COC$\underline{H}$₂Br), 6.83 (1H, s, —C$\underline{H}$Ph₂).

PREPARATION 3

Production of the starting material, 4-bromo-3-oxobutyric acid diphenylmethyl ester (2b) by an alternative route.

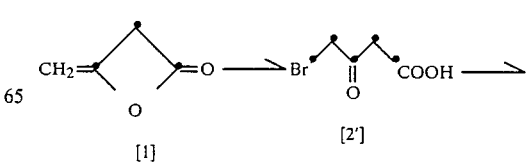

-continued

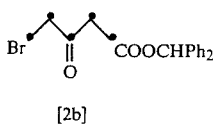
[2b]

(1) 4-bromo-3-ketobutyric acid.

To a solution of diketone (1) (43.5 g, 0.518 moles) in dry dichloromethane (200 ml) is added a solution of bromine (82.7 g, 0.518 moles) in anhydrous dichloromethane (100 ml) dropwise over 40 minutes period at −30° C. to −40° C. After stirring at room temperature for 30 minutes, the reaction mixture is poured into ice water. The separated crystals are collected by filtration and dissolved in ethyl acetate. The solution is extracted with aqueous sodium hydrogen carbonate. The extract is neutralized with hydrochloric acid to separate crystals of the title compound. Yield: 67.5 g, 55%. A part of the crystals is recrystallized from a mixture of dichloromethane and n-hexane to show the melting point 76° C. to 78° C. as white crystals.

IR (Nujol): 1730, 1700 cm$^{-1}$.

NMR (EM-390, CDCl$_3$, δ): 3.74 (2H, s, —CH$_2$COOH), 4.34 (2H, s, —COCH$_2$Br), 9.62 (1H, brs, —COOH).

(2) Production of the compound (2b)

The β-ketoacid (2') obtained according to the method of above (1) (15 g, 82.6 millimole) is dissolved in anhydrous dichloromethane (220 ml) and mixed with a solution of diphenyldiazomethane in anhydrous dichloromethane (70 ml) under ice cooling. The addition is stopped when the reaction mixture turned pale red. The mixture is concentrated under reduced pressure to remove the solvent to leave the compound (2b) in nearly quantitative yield. This product is the same with that of Preparation 2 above when compared with physicochemical data.

PREPARATION 4

Production of the starting material, 3-phenyl-7-oxo-6-t-butyl-dimethylsilyl-2,6-diaza-4-oxabicyclo[3.2.0]heptane (6).

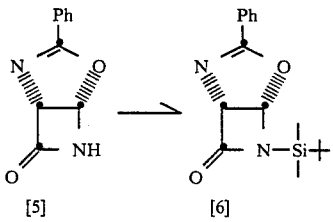
[5]  [6]

To a suspension of 3-phenyloxazolinoazetidinone (5) (1.0 g, 5.31 millimole) in anhydrous dichloromethane (15 ml) are added triethylamine (1.11 ml, 7.97 millimole) and t-butyl-dimethylsilyl chloride (1.21 g, 7.97 millimole), and the mixture is stirred at room temperature over 1 to 1.5 hours. After the suspension turned clear, the stirring is continued for further 30 minutes. The reaction mixture is washed with water and saline, dried over magnesium sulfate, filtered and concentrated under reduced pressure to remove the solvent leaving crystalline title silyl compound (6, 1.6 g, Yield: about 100%).

IR (CHCl$_3$): 1765, 1635, 1602, 1580, 1326, 1170, 846, 826 cm$^{-1}$.

NMR (EM-390, CDCl$_3$, δ): 0.27 and 0.31 (6H, s, —Si(t-Bu)(CH$_3$)$_2$), 0.93 (9H, s, —Si(t-Bu)(CH$_3$)$_2$), 5.37 (1H, d, J=3.1 Hz, Ha (see below)), 5.83 (1H, d, J=3.1 Hz, Hb (see below)), 7.2–7.6 (3H, m, aromatic proton), 7.9–8.1 (2H, m, aromatic proton).

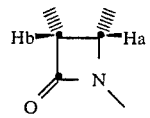

EXAMPLE 1

Production of 7-benzamido-3-hydroxy-8-oxo-5-oxa-1-azabicyclo[4.2.0]oct-2-en-2-carboxylic acid ethyl ester (10a)

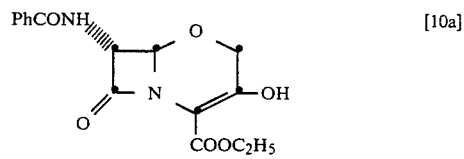
[10a]

(1) Production of 4-hydroxy-3-ketobutyric acid ethyl ester (3a).

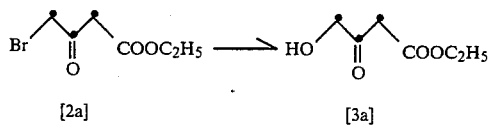
[2a]  [3a]

To a solution of 4-bromo-3-ketobutyric acid ethyl ester (2a) (21 g, 0.10 moles) in methanol dried prior to use with Molecular Sieves is added sodium formate (10.2 g, 0.15 moles), and the mixture is refluxed for 1 hour. The reaction mixture is concentrated under reduced pressure to remove the solvent. The residue is extracted with chloroform. The extract is purified by silica gel column chromatography (eluting solvent=benzene/ethyl acetate (2:1)) to give the title compound (3a). Yield: 7.34 g, 50%.

IR (CHCl$_3$): 3500, 1740, 1725 cm$^{-1}$.

NMR (EM-390, CDCl$_3$, δ): 1.27 (3H, t, J=7.5 Hz, —CH$_2$CH$_3$), 3.38 (1H, brs, —CH$_2$OH), 3.51 (2H, s, —CH$_2$COOC$_2$H$_5$), 6.21 (2H, q, J=7.5 Hz, —CH$_2$CH$_3$), 6.38 (2H, brs, —CH$_2$OH).

(2) Production of 2-diazo-4-hydroxy-3-oxobutyric acid ethyl ester (4a).

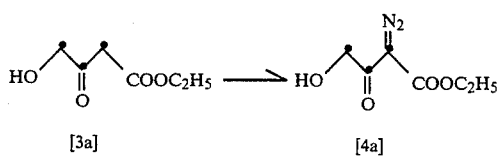
[3a]  [4a]

The compound (3a) obtained by the method of above (1) (1.02 g, 7.0 millimole) is dissolved in acetonitrile (10 ml), cooled with ice, and mixed with triethylamine (1.07 ml, 7.7 millimole). The mixture turns dark brown. To this solution is added p-toluenesulfonyl azide (1.52 g, 7.7 millimoles) in acetonitrile (4 ml) over 5 minutes, and the mixture is stirred for 1 hour at room temperature. The reaction mixture is concentrated under reduced pressure and the residue is extracted with ether. The extract is chromatographed over Lobar ® column (silica gel column D for high precision liquid chromatography distributed by E. Merck, A. G.) and eluted with a mixture of n-hexane and acetone (2:1). The eluate is recrystallized from n-hexane to give the crystalline title compound (901 mg, 75%). m.p. 53°–54° C.

IR (CHCl$_3$): 3450, 2140, 1723, 1700, 1655 cm$^{-1}$.

NMR (EM-390, CDCl$_3$, δ): 1.33 (3H, t, J=7.5 Hz, —COOCH$_2$CH$_3$), 3.50 (1H, brs, —OH), 4.32 (2H, q, J=7.5 Hz, —COOCH$_2$CH$_3$), 4.62 (2H, brs, —CH$_2$OH).

(3) Production of 3α-benzamido-4β-(3-carbethoxy-2-oxo-propoxy)-1-t-butyldimethylsilyl-2-azetidinone (7a).

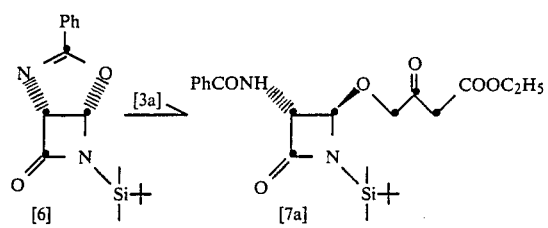

The compound (6) produced by the method of Preparation 4 (1.12 g, 3.70 millimoles) and the compound (3a) produced by the method of above 1) (1.18 g, 7.40 millimoles) are mixed together, heated at 45° C. to give resin (solidifies by cooling to room temperature), mixed with boron trifluoride etherate (24 μl, 0.05 molar equivalents), and stirred for 1 hour at 45° C. The reaction mixture is dissolved in ethyl acetate, poured into ice water containing sodium hydrogen carbonate and extracted with ethyl acetate. The extract solution is washed with water, dried and evaporated to give crude title compound (7a). This is purified by Lobar ® column (eluting solvent=benzene/ethyl acetate (9:1)) to give pure sample (970 mg, 58%). A part of the sample is crystallized from a mixture of ether and petroleum ether to give white crystals melting at 94° to 95° C.

IR (CHCl$_3$): 3430, 1750 (broad), 1666, 1602, 1581, 844, 826 cm$^{-1}$.

IR (Nujol): 3340, 1734 (broad), 1652, 1600, 1578, 1316, 840 cm$^{-1}$.

NMR (EM-390, CDCl$_3$, δ): 0.29 and 0.32 (6H, s, —Si(t-Bu)(CH$_3$)$_2$), 1.00 (9H, s, —Si(t-Bu)(CH$_3$)$_2$), 1.23 (3H, t, J=7.5 Hz, —COOCH$_2$CH$_3$), 3.52 (2H, s, —COCH$_2$COOC$_2$H$_5$), 4.16 (2H, q, J=7.5 Hz, —COOCH$_2$CH$_3$), 4.62 (2H, s, —OCH$_2$CO—), 4.70 (1H, d, J=6.0 Hz, Ha (see below)), 4.91 (1H, s, Hb (see below)), 7.3–7.6 (3H, m, aromatic proton), 7.70 (1H, d, J=6.0 Hz, —CONH—), 7.7–7.9 (2H, m, aromatic proton).

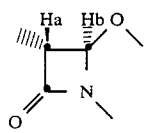

The same reaction can be carried out in ethyl acetate or dichloromethane (10 weights each).

(4) Production of 3α-benzamido-1-t-butyldimethylsilyl-4β-(3-carboethoxyl-3-diazo-2-oxopropoxy)-2-azetidinone (8a)

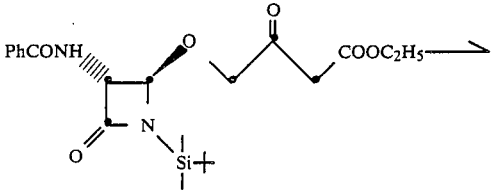

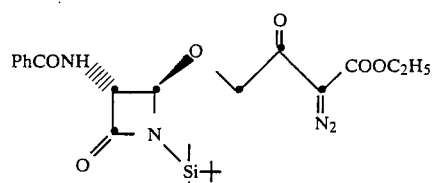

To a solution of the compound (7a, 99 mg, 0.22 millimoles) in anhydrous acetonitrile (1 ml) are added triethylamine (33 μl, 0.24 millimoles) and p-toluenesulfonyl azide (49 mg, 0.24 millimole) in anhydrous acetonitrile (0.2 ml) under ice cooling. The mixture is stirred at room temperature for 1.5 hours, concentrated under reduced pressure, and dissolved in ether. The ether solution is washed with aqueous sodium hydrogen carbonate and water, dried over magnesium sulfate and concentrated under reduced pressure to give the crude title compound (8a). The product is purified by chromatography over Lobar ® column B and a mixture of benzene and ethyl acetate (2:1) as eluting solvent affording pure product (8a, 86 mg, 82%).

IR (CHCl$_3$): 3430, 2140, 1756, 1714, 1664, 1601, 1580, 1316, 843, 828 cm$^{-1}$.

NMR (EM-390, CDCl$_3$, δ): 0.31 and 0.32 (6H, s, —Si(t-Bu)(CH$_3$)$_2$), 1.00 (9H, s, —Si(t-Bu)(CH$_3$)$_2$), 1.29 (3H, t, J=7.5 Hz, —COOCH$_2$CH$_3$), 4.27 (2H, q, J=7.5 Hz, —COOCH$_2$CH$_3$), 4.69 (1H, d, J=6.0 Hz, Ha (see below)), 4.88 and 4.99 (2H, ABq, J=18 Hz), 5.10 (1H, s, Hb (see below)), 7.3–7.5 (3H, m, aromatic proton), 7.65 (1H, d, J=6.0 Hz, —CONH—), 7.7–7.9 (2H, m, aromatic proton).

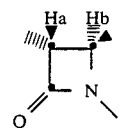

(5) Alternative synthesis of the compound (8a).

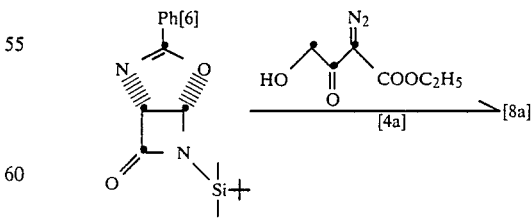

To a solution of the compound (6, 160 mg) and compound (4a, 109.3 mg, 0.635 millimoles) in ethyl acetate (0.5 ml) is added boron trifluoride etherate (6.6 μl, 0.0529 millimoles), and the mixture is stirred at room temperature for 1 hour. The reaction mixture is diluted with ethyl acetate, washed with aqueous sodium hydrogen carbonate, water and saline, dried over magnesium sulfate and concentrated under reduced pressure to remove the solvent. The residue is purified by chromatography over Lobar ® column B using a mixture of benzene and ethyl acetate (4:1) as eluting solvent to afford the compound (8a, 188 mg, 75%). This product is identified with the product of 5) by comparing the physicochemical constants.

(6) Production of 3α-benzamido-4-(3-carbethoxy-3-diazo-2-oxopropoxy)-2-azetidinone (9a).

To a solution of the compound (8a) (100 mg, 0.211 millimoles) in a mixture of ethanol (2 ml) and water (0.25 ml) is added 1N-hydrochloric acid in ethanol (0.63 ml, 3 molar equivalents), and the mixture is stirred under ice cooling for 15 hours. A part of the title compound (9a) separates during the reaction. The reaction mixture is diluted with water (10 ml), stirred for 30 minutes and filtered to collect the separated crystals. The crystals are washed with cold methanol and dried to give the compound (9a, 65 mg, 86%). m.p. 170°–171° C.

IR (Nujol): 3310, 2140, 1778, 1702, 1664, 1645, 1580 cm$^{-1}$.

NMR (EM-390, CDCl$_3$:CD$_3$OD=1:1 δ): 1.33 (3H, t, J=7.5 Hz, —COOCH$_2$C$\underline{H}_3$), 4.32 (2H, q, J=7.5 Hz, —COOC$\underline{H}_2$CH$_3$), 4.72 (1H, s, Ha (see below)), 4.82 (2H, s, —OC$\underline{H}_2$CO—), 5.30 (1H, s, Hb (see below)), 7.4–8.0 (5H, m, aromatic proton).

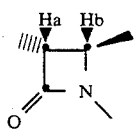

(7) Production of the objective compound (10a)

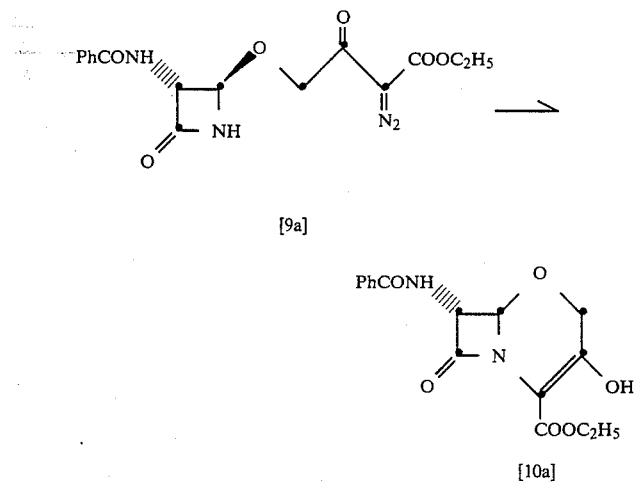

To a suspension of the compound (9a) (50 mg, 0.139 millimoles) in anhydrous benzene (1.5 ml) is added dirhodium tetraacetate (Rh$_2$(OAc)$_4$) 0.6 mg, 1.0 mole percent), and the mixture is refluxed for 30 minutes. On heating, nitrogen evolves and the mixture turns clear). The reaction mixture is diluted with ethyl acetate, washed with water and saline, dried and concentrated to leave crystalline residue (40 mg, 87%). This is recrystallized from a mixture of methanol and ether to give the objective compound (10a) melting at 155° to 158° C.

IR (CHCl$_3$): 3430, 3310, 1776, 1666, 1625, 1578, 1505, 1480, 1330 cm$^{-1}$.

NMR ($^1$H, EM-360, CDCl$_3$, δ): 1.36 (3H, t, J=7.5 Hz, —COOCH$_2$C$\underline{H}_3$), 4.36 (2H, q, J=7.5 Hz, —COOC$\underline{H}_2$CH$_3$), 4.43 (2H, s, C$_2$—2H), 4.93 (1H, d, J=7.0 Hz, C$_{7\beta}$—H), 5.09 (s, 1H, C$_{6\alpha}$—H), 7.15 (1H, d, J=7.0 Hz, —CON$\underline{H}$—), 7.3–7.9 (5H, m, aromatic proton), 11.01 (1H, brs, —OH).

$^{13}$C-NMR (XL-100A, CDCl$_3$, δ): 14.2 (—COOCH$_2$$\underline{C}$H$_3$), 62.1 (—COO$\underline{C}$H$_2$CH$_3$), 63.9 (C$_7$), 64.0 (C$_2$), 83.10 (C$_6$), 104.3 (C$_4$), 127.3 (C$_b$) (see below for C$_b$ to C$_e$), 128.7 (C$_c$), 132.2 (C$_d$), 132.8 (C$_e$), 160.3 (C$_3$), 163.0 (C$_8$), 166.5 (—$\underline{C}$OOCH$_2$CH$_3$), 167.6 (—$\underline{C}$ONH—).

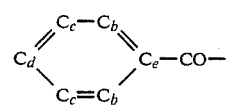

Mass (m/e): 332 (M+).

EXAMPLE 2

Production of 7-benzamido-3-hydroxy-8-oxo-5-oxa-1-azabicyclo[4.2.0]oct-2-en-2-carboxylic acid diphenylmethyl ester (10b).

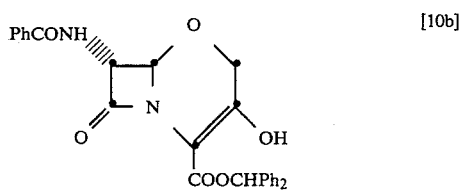

(1) Production of 4-hydroxy-3-ketobutyric acid diphenylmethyl ester (3b)

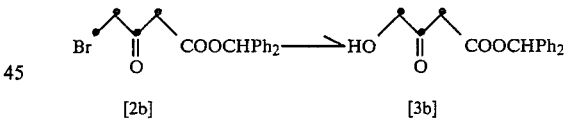

To a solution of 4-bromo-3-ketobutyric acid diphenylmethyl ester (2b, 11.4 g, 32.8 millimoles) in methanol dried with Molecular Sieves is added sodium formate (3.40 g, 50.0 millimoles), and the mixture is refluxed for 4 hours. The reaction mixture is filtered to remove solid material concentrated under reduced pressure, and extracted with ethyl acetate. The extract is washed with water, dried over magnesium sulfate and evaporated to remove the solvent. The residue is purified by chromatography over Lobar ® column B using a mixture of benzene and ethyl acetate (3:1) as eluting solvent to afford the title compound (3b, 4.39 g, 47%).

IR (CHCl$_3$): 3500, 1740, 1725 cm$^{-1}$.

NMR (EM-390, CDCl$_3$, δ): 3.05 (1H, brs, —OH), 3.52 (2H, s, —COC$\underline{H}_2$COCHPh$_2$), 4.24 (2H, s, —C$\underline{H}_2$OH), 6.91 (1H, s, —C$\underline{H}$Ph$_2$), 7.2–7.4 (10H, m, aromatic proton).

(2) Production of 2-diazo-4-hydroxy-3-ketobutyric acid diphenylmethyl ester (4b).

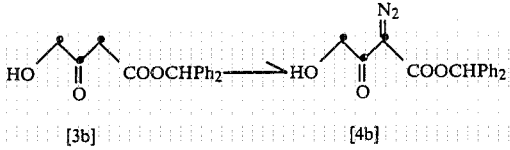

The compound (3b) obtained above (1.4 g, 4.92 millimoles) is dissolved in anhydrous acetonitrile (14 ml) and mixed with triethylamine (0.75 ml, 5.30 millimoles) and then a solution of p-toluenesulfonyl azide (1.05 g, 5.30 millimoles) in anhydrous acetonitrile (5 ml) over 10 minutes with stirring. After the addition, the mixture is stirred for 50 minutes at room temperature and concentrated under reduced pressure. The residue is extracted with ether. The extract is washed with cold aqueous potassium hydroxide (A solution of KOH 2 g in water 30 ml and KOH 1 g in water 20 ml) and then water, dried over magnesium sulfate and concentrated to remove the solvent to give the crude title compound. This is purified by chromatography over Lobar ® column B using a mixture of benzene and ethyl acetate (4:1) as eluting solvent to afford the compound (4b, 1.15 g, 75%).

IR (CHCl$_3$): 3470, 2140, 1720, 1660 cm$^{-1}$.

NMR (EM-390, CDCl$_3$, δ): 3.37 (1H, t, J=5.0 Hz, —OH), 4.61 (2H, d, J=5.0 Hz, —COCH$_2$OH), 7.03 (1H, s, —CHPh$_2$), 7.2–7.5 (10H, m, aromatic proton).

(3) Production of 3α-benzamido-1-t-butyldimethylsilyl-4β-(3-diphenylmethoxycarbonyl-3-diazo-2-oxopropoxy)-2-azetidinone (8b).

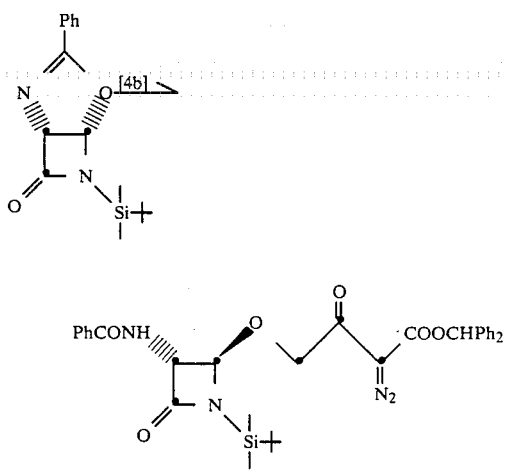

To a solution of the compound (6, 275 mg, 0.909 millimoles) obtained by the method of Preparation 4 and the compound (4b, 338 mg, 1.09 millimoles) obtained by the method of above 2) in dry ethyl acetate (0.85 ml) is added boron trifluoride etherate (0.68 μl, 0.0545 millimoles), and the mixture is stirred at room temperature for 1 hour. The reaction mixture is diluted with ethyl acetate, washed with water, aqueous 5% sodium hydrogen carbonate and water, dried over magnesium sulfate and concentrated under reduced pressure to give the crude title compound. This is purified by chromatography over Lobar ® column B using a mixture of cyclohexane and ethyl acetate (4:1) as eluting solvent to afford pure compound (8b, 472 mg, 71%).

IR (CHCl$_3$): 3430, 2140, 1758, 1720, 1670, 1600, 1300, 843 cm$^{-1}$.

NMR (EM-390, CDCl$_3$, δ): 0.30 and 0.34 (6H, s, —Si(t-Bu)(CH$_3$)(CH$_3$)$_2$), 0.97 (9H, s, —Si(t-Bu)(CH$_3$)$_2$), 4.68 (1H, d, J=6.0 Hz, Ha (see below)), 4.84 and 5.04 (2H, ABq, J=18 Hz, —OCH$_2$COC(N$_2$)—), 5.08 (1H, s, Hb), 6.69 (1H, s, —CHPh$_2$), 7.2–7.9 (10H, m, aromatic proton).

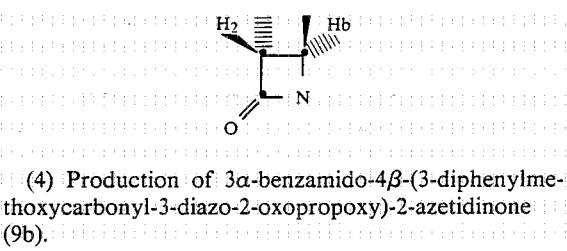

(4) Production of 3α-benzamido-4β-(3-diphenylmethoxycarbonyl-3-diazo-2-oxopropoxy)-2-azetidinone (9b).

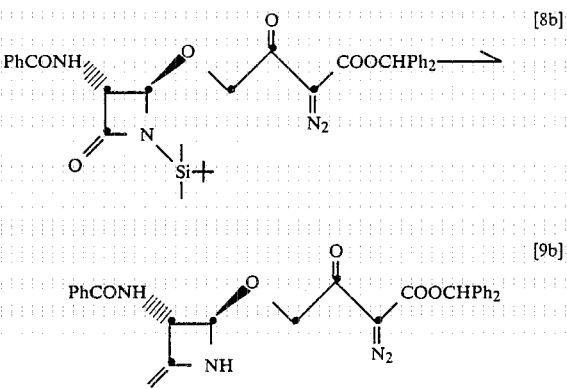

To a solution of the compound (8b, 165 mg, 0.269 millimoles) in methanol (3.3 ml) are added water (0.4 ml), and 1N-hydrogen chloride in methanol (0.807 ml, 0.807 millimoles) under ice cooling, and the mixture is stirred at room temperature for 3 hours. White crystals appears after about 1 hour's reaction. Then ether is added under ice cooling and the crystals are collected by filtration. The obtained crystals are washed with ether and dried in vacuo over phosphorus pentaoxide to give the title compound (9b, 114 mg, 85%). m.p. 182°–186° C.

IR (Nujol): 3310, 2150, 1784, 1696, 1642 cm$^{-1}$.

(5) Production of the objective compound (10b)

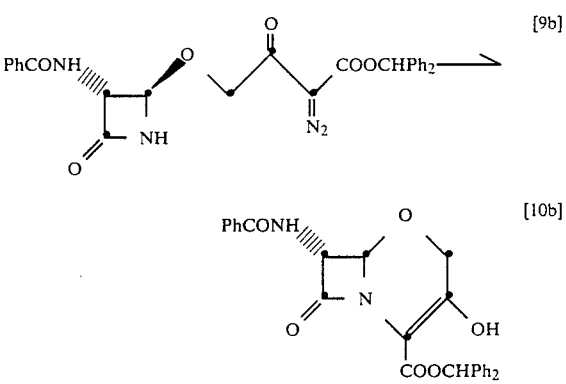

To a suspension of the compound (9b, 95 mg, 0.191 millimoles) in benzene (3 ml) is added dirhodium tetraacetate (1.1 mg, 0.0024 millimoles), and the suspension is heated. Nitrogen evolves and crystals disappears to give clear solution after 3 minutes. The refluxing is continued for further 30 minutes and then diluted with ethyl acetate and washed with water and saline. The mixture is dried over magnesium sulfate and concentrated under reduced pressure to remove the solvent. The residue is dissolved in a mixture of benzene and ethyl acetate (1:1), treated with silica gel (1 g), filtered and concentrated to remove the solvent giving the objective compound (10b, 90 mg, ca. 100%).

IR (CHCl$_3$): 3430, 1780, 1674, 1620, 1270 cm$^{-1}$.

$^1$H-NMR (EM-390, CDCl$_3$, δ): 4.31 (2H, brs, C$_2$—2H), 4.98 (1H, s, C$_{6α}$—H), 5.00 (1H, d, J=7.5 Hz, C$_{7β}$—H), 6.96 (1H, s, —CHPh$_2$), 7.1–7.8 (10H, m, aromatic proton), 10.96 (1H, brs, OH).

$^{13}$C-NMR (XL-100A, CDCl$_3$, δ): 63.7 (C-7), 64.0 (C-2), 79.0 (—COOCHPh$_2$), 83.1 (C-6), 104.1 (C-4), 161.1 (C-3), 163.0 (C-8), 165.6 (COOCHPh$_2$), 167.6 (—CONH—).

EXAMPLE 3

Production of 7α-benzamido-3-methylene-1-dethia-1-oxacepham-4α-carboxylic acid ethyl ester (10c).

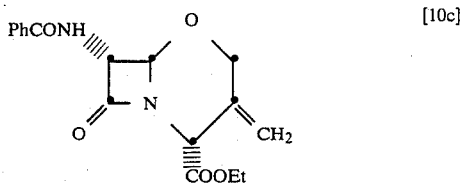

(1) Production of 2-hydroxyiminoacetoacetic acid ethyl ester (4-IIc)

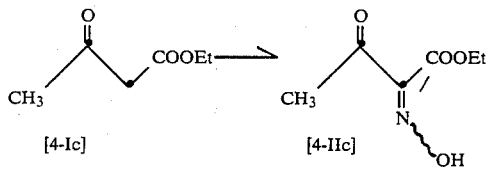

To an ice cooled solution of ethyl acetoacetate (4-Ic, 36.5 g, 0.281 mole) in glacial acetic acid (42 ml) (up to 5° C.) is added a solution of sodium nitrite (22.5 g, 0.321 mole) in water (50 ml) dropwise over 20 minutes. The solution warms up to 25° C. due to exothermic reaction. Then, water (150 ml) is added thereto and the stirring is continued for 2 hours. The reaction mixture is extracted with ether. The extract solution is washed with water, cold aqueous sodium hydrogen carbonate and saline, dried over magnesium sulfate and freed from the solvent by concentration under reduced pressure. The residue is crystallized from a mixture of toluene and petroleum ether to give the compound (4-IIc, 36.5 g, 82%).

IR (CCl$_4$): 3540, 3320 (broad), 1750, 1723, 1705, 1685, 1625, 994 cm$^{-1}$.

NMR (EM-390 (90 MHz), δ): 1.33 (3H, t, J=7.5 Hz, —COOCH$_2$CH$_3$), 2.41 (3H, s, —COCH$_3$), 4.39 (2H, q, —COOCH$_2$CH$_3$).

(2) Production of 2-t-butyldimethylsilyloxyimino-3-t-butyldimethylsilyloxy-3-butenoic acid ethyl ester (4-IIIc)

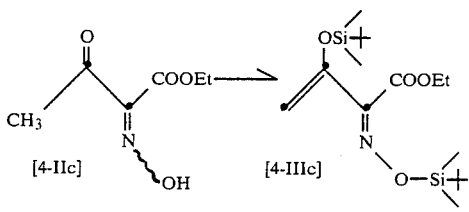

To a solution of lithium bis-trimethylsilylamide in tetrahydrofuran (134 ml) prepared from bistrimethylsilylamine (41 ml) and n-butyllithium cooled at −75° C. is added a solution of the compound (4-IIc, 10.0 g, 62.83 millimoles) in tetrahydrofuran (50 ml) at −69° to −71° C. over 45 minutes dropwise, and the mixture is stirred for 1 hour at −70° C. To the reaction mixture was added t-butyldimethylsilyl chloride (29.6 g, 0.196 moles) in tetrahydrofuran (50 ml) solution at −70° C. over 30 minutes dropwise and N,N,N',N'-tetramethylethylenediamine (29 ml) at −70° C. dropwise over 15 minutes. The mixture is stirred at −70° C. for 1 hour and at 3° C. for 1 hour 20 minutes. The reaction mixture is diluted dropwise with cold water (50 ml) at a temperature lower than 10° C. and then extracted with ether. The extract solution is washed with saline, neutralized with 1N-cold hydrochloric acid to pH 7.4 (from pH 11.5 measuring with a pH meter), washed with saline, sodium hydrogen carbonate and saline, dried over magnesium sulfate and concentrated under reduced pressure to remove the solvent affording the crude compound (4-IIIc, 25.4 g).

IR (film): 1741, 1605, 1250, 1098, 966, 840, 784 cm$^{-1}$.

(3) Production of 4-t-butyldimethylsilyl-2-t-butyldimethylsilyloxyiminoacetoacetic acid ethyl ester (4-IVc)

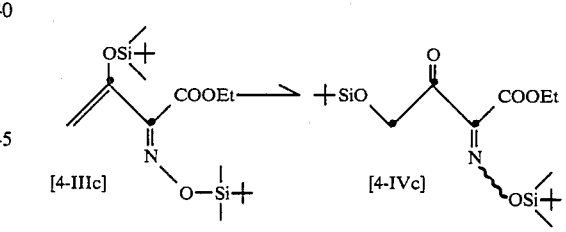

A solution of the crude compound (4-IIIc, 24.3 g, 60.11 millimoles) in chloroform (360 ml) is cooled with ice water. To this solution is added sodium hydrogen carbonate (9.95 g) and a solution of m-chloroperbenzoic acid (20.1 g, 99.2 millimoles) in chloroform (240 ml) dropwise over 20 minutes at 5° C. to 8° C. The mixture is stirred for further 16 hours under ice cooling. The reaction mixture is poured into cold 10% sodium sulfite aqueous solution and extracted with chloroform. The extract solution is washed with aqueous sodium hydrogen carbonate and saline, dried over magnesium sulfate and concentrated under reduced pressure to remove the solvent to give oily material (27.7 g). This is chromatographed over silica gel (150 g, elution with benzene) to give cis-trans mixture of the compound (4-IVc) 14.7 g, 58%).

IR (film): 1748, 1720, 1598, 1253, 1211, 993, 955, 832, 783 cm$^{-1}$.

NMR (EM-390 (90 MHz), CDCl₃, δ): 0.18 (12H, s, 2x —Si(t-Bu)(C$\underline{H}$₃)₂), 0.91 and 0.95 (18H, s, 2x —Si(t-Bu)(CH₃)₂), 1.32 (3H, t, J=7.5 Hz, —COOCH₂C$\underline{H}$₃), 4.32 (2H, q, J=7.5 Hz, —COOC$\underline{H}$₂CH₃), 4.65 (2H, s, —OC$\underline{H}$₂CO—).

(4) Production of 3-t-butyldimethylsilyloxymethyl-2-t-butyldimethylsilyloxyimino-3-butenoic acid ethyl ester (4-Vc).

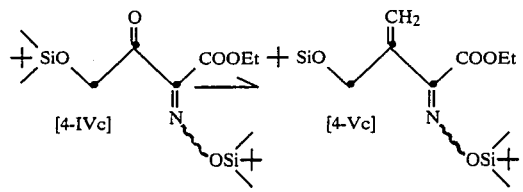

To a suspension of methyl-triphenylphosphonium bromide (Ph₃P⁺CH₃Br⁻, 11.1 g, 31.1 millimoles) in ether (165 ml) is added n-butyl lithium over 20 minutes. After stirring for 30 minutes, the mixture is cooled at 5° C. with ice water and mixed with the compound (4-IVc, 14.7 g, 36.4 millimoles) in ether (150 ml) at 5° C. dropwise over 35 minutes. The mixture is stirred for 15 minutes, diluted with hexamethylphosphorotriamide (15.6 ml) at 3° C., and the mixture is stirred at 5° C. for 1 hour 40 minutes. This reaction mixture is diluted with saturated ammonium chloride aqueous solution (150 ml) at 10° C. over 10 minutes. Aqueous layer is extracted with ether and the extract solution is washed with saturated ammonium chloride, saturated sodium hydrogen carbonate solution and saline, dried over magnesium sulfate and concentrated under reduced pressure to leave oily material (13.7 g). This is purified by chromatography over silica gel (160 g) using dichloromethane as eluting solvent to afford a cis, trans-mixture of the compound (4-Vc, 7.02 g, 48%).

IR (film): 1740, 1640, 1258, 1124, 1070, 976, 840, 789 cm⁻¹.

NMR (T-60 (60 MHz), CDCl₃, δ): 0.09 (6H, s, —C-Si(t-Bu)—(C$\underline{H}$₃)₂), 0.17 (6H, s, =NOSi(t-Bu)(C$\underline{H}$₃)₂), 0.93 (18H, s, 2x t-Bu), 1.33 (3H, t, J=7.5 Hz, —COOCH₂C$\underline{H}$₃), 4.32 (2H, q, J=7.5 Hz, —COOC$\underline{H}$₂CH₃), 4.38 (2H, broad, —OC$\underline{H}$₂C(=CH₂)—), 5.28 (1H, broad,

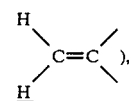

5.77 (1H, broad,

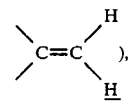

(5) Production of 3-hydroxymethyl-2-oxyimino-3-butenoic acid ethyl ester (4-VIc).

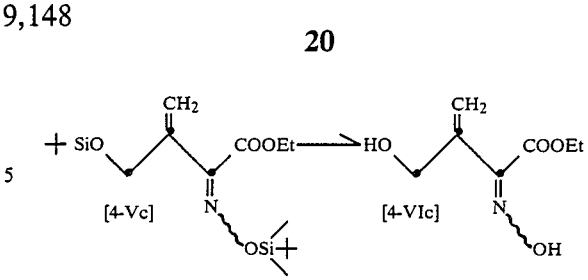

To a solution of the compound (4-Vc, 4.70 g, 11.7 millimoles) in a mixture of ether (90 ml) and water (12 ml) is added a solution of hydrogen chloride in ethanol (58.5 ml, 5 molar equivalents) at cold, and the mixture is stirred under ice cooling for 17 hours. The reaction mixture is concentrated to a third or fifth volume, diluted with ice water and extracted with chloroform. The extract solution is washed with saline, dried over magnesium sulfate and concentrated under reduced pressure to remove the solvent to afford the crude compound (4-VIc). This is purified by chromatography over Lobar ® column C using a mixture of benzene and ethyl acetate (2:1) as eluting solvent to afford the objective material (1.82 g, 90%). A part of this is recrystallized from a mixture of ether and n-pentane to afford crystals melting at 38° C. to 45° C.

| Elemental analysis: | C | H | N |
|---|---|---|---|
| Calcd. (%) | 48.55 | 6.40 | 8.09 |
| Found (%) | 47.12 | 6.20 | 7.79 |

IR (CHCl₃): 3570, 3270 (broad), 1740, 1630, 1092, 1032 cm⁻¹.

NMR (EM-390 (90 MHz), CDCl₃, δ): 1.33 (3H, t, J=7.5 Hz, —COOCH₂C$\underline{H}$₃), 4.36 (2H, s, —C$\underline{H}$₂OH), 4.37 (2H, q, J=7.5 Hz, —COOC$\underline{H}$₂CH₃), 5.29 (1H, s,

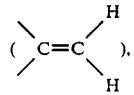

9.5–10.3 (1H, broad s, =N—OH).
Mass: M⁺ 173.

¹³C-NMR (XL-100, CDCl₃): 14.1 (—COOCH₂$\underline{C}$H₃), 62.1 (—$\underline{C}$H₂OH and —COO$\underline{C}$H₂CH₃), 120.0

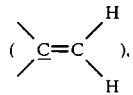

139.1

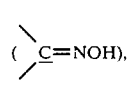

151.7

( \$\underline{C}$=NOH), (6) Production of 2-diazo-3-hydroxymethyl-3-butenoic acid ethyl ester (4c).

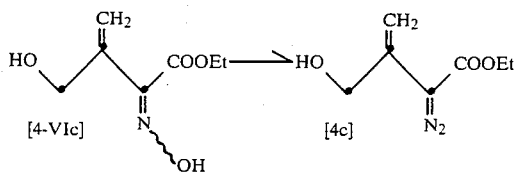

To a solution of the compound (4-VIc, 1.0 g, 5.78 millimoles) in dichloromethane (20 ml) cooled at −40° C. is added a solution of n-butyllithium in hexane (1.1 molar equivalent), and the mixture is stirred at the same temperature for about 15 minutes. The reaction mixture is warmed up to −20° C. To this solution is added dropwise a solution of O-mesitylenesulfonylhydroxylamine (1.06 g 5.78 millimoles) in dichloromethane (10 ml) over 30 minutes, and the mixture is stirred for 30 minutes at the same temperature and at 0° C. for 30 minutes, poured into ice water and extracted with ether. The extract solution is washed with saline, dried over magnesium sulfate and concentrated under reduced pressure. The residue is purified by chromatography over Lobar® column B using a mixture of benzene and ethyl acetate (2:1) to afford the objective compound (4c, 442 mg, 45%).

IR (CHCl₃): 3599, 2120, 1740, 1602 cm⁻¹.

NMR (EM-390 (90 MHz), CDCl₃, δ): 1.33 (3H, t, J=7.5 Hz, —COOCH₂C$\underline{H}$₃), 4.36 (2H, s, —C$\underline{H}$₂OH), 4.37 (2H, q, J=7.5 Hz, —COOC$\underline{H}$₂CH₃), 5.32 (1H, brs,

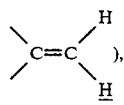), 5.84 (1H, brs,

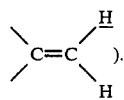).

(7) Production of 3α-benzamido-4β-(3-carbethoxy-3-diazo-2-methylenepropyl)oxy-1-t-butyldimethyl-silylazetidin-2-one (8c).

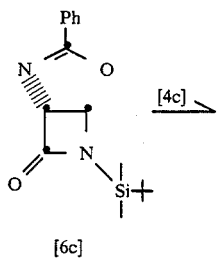

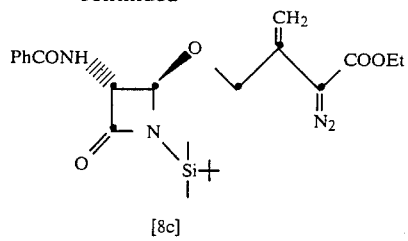

To a solution of the compound (4c, 100 mg, 0.588 millimole) and the compound (6c, 178 mg, 0.588 millimoles) in ethyl acetate (3 ml) is added boron trifluoride etherate (0.05 molar equivalents), and the mixture is stirred at room temperature for 1 hour. The reaction mixture is diluted with ethyl acetate, washed with aqueous sodium hydrogen carbonate and saline, and concentrated under reduced pressure to remove the solvent. The residue is purified by chromatography over Lobar® column B using a mixture of benzene and ethyl acetate (2:1) to afford the compound (8c, 94 mg, 60%).

IR (CHCl₃): 3430–3350, 2120, 1760, 1739, 1661, 601 cm⁻¹.

NMR (XL-100A (100 MHz), CDCl₃, δ): 0.28 (6H, s, —Si(t-Bu) (C$\underline{H}$₃)₂), 1.34 (3H, t, J=7.0 Hz, —COOCH₂C$\underline{H}$₃), 4.39 (2H, q, J=7.0 Hz, —COOC$\underline{H}$₂CH₃), 4.4–4.6 (2H, m, —OC$\underline{H}$₂—), 4.75 (1H, d, J=7.0 Hz, C₇—$\underline{H}$), 5.04 (1H, s, C₆—$\underline{H}$), 5.46 and 5.84 (1H, brs, olefinic proton), 7.15 (1H, d, J=7.0 Hz, —CON$\underline{H}$—), 7.3–7.9 (5H, m, aromatic proton).

(8) Production of 3α-benzamido-4β-(3-carbethoxy-3-diazo-2-methylenepropyl)oxyazetidin-2-one (9c).

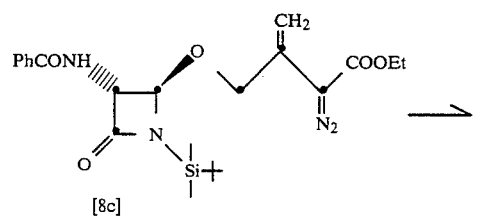

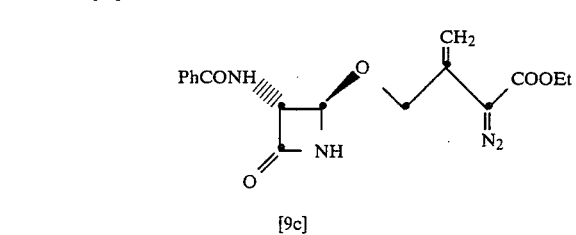

To a solution of the compound (8c, 90 mg, 0.190 millimoles) in a mixture of ethanol (2 ml) and water (0.25 ml) is added 1N-hydrogen chloride in ethanol (3 molar equivalents), and the mixture is stirred for 10 hours under ice cooling. White precipitate separates during the reaction. The reaction mixture is diluted with water (5 ml), stirred for 30 minutes, and filtered to collect the white precipitate. The precipitate is washed with cold ethanol and dried to give the compound (9c, 68 mg, 80%).

IR (Nujol): 3310, 2120, 1772, 1695, 1640 cm⁻¹.

(9) Production of 7α-benzamido-3-methylene-1-dethia-1-oxacepham-4α-carboxylic acid ethyl ester (10c).

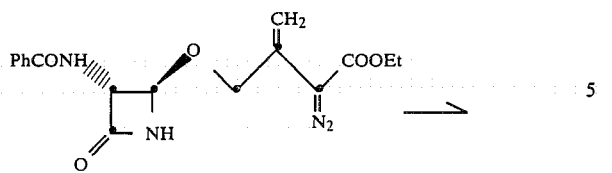

[9c]

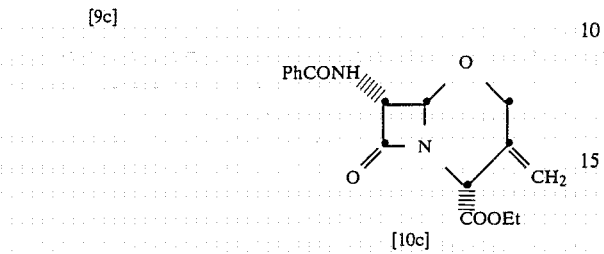

[10c]

To a solution of the compound (9c, 60 mg, 0.167 millimoles) in a mixture (3 ml) of benzene and dichloromethane (1:1) is added dirhodium tetraacetate (1 molar per-cent) and the mixture is refluxed for 45 minutes. The reaction mixture is diluted with ethyl acetate (10 ml), washed with water and saline, and dried over magnesium sulfate. The solvent is evaporated off under reduced pressure. The residue is purified by chromatography over silica gel (3 g) using a mixture of benzene and ethyl acetate (2:1) as eluting solvent to give the compound (10c, 48 mg, 87%).

IR (CHCl$_3$): 3440, 1770, 1735, 1668, 1660 cm$^{-1}$.

NMR (EM-390 (90 MHz), CDCl$_3$, δ): 1.20 (3H, t, J=7.5 Hz, —COOCH$_2$CH$_3$), 4.13 (2H, q, J=7.5 Hz, —COOCHCH), 4.29 (2H, brs, C—2H), 4.97 (1H, d, J=7.0 Hz, C$_7$—H), 5.02 (1H, s, C$_4$—H), 4.21 and 4.25 (2H, s, olefinic proton), 4.34 (1H, brs, C$_6$—H), 7.2–7.5 and 7.7–7.9 (5H, m, aromatic proton).

EXAMPLE 4

Alternative synthesis of 7α-benzamido-3-methylene-1-dethia-1-oxacepham-4α-carboxylic acid ethyl ester (10c).

(1) Production of an oxime (8-Ia).

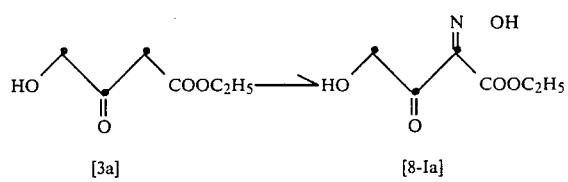

[3a]     [8-Ia]

To a solution of the compound (3a, 21.9 g, 0.15 mole) in glacial acetic acid (23 ml) is added an aqueous solution (27 ml) of sodium nitrite (11.8 g, 0.171 moles) dropwise under stirring at 10° C. over 30 minutes period. The mixture is stirred at room temperature for 1 hour, diluted with ice water and extracted with a mixture of methyl ethyl ketone and ethyl acetate (1:1). The extract solution is washed with saline, cold 1N-sodium hydroxide aqueous solution and saline, dried over magnesium sulfate and concentrated to remove the solvent affording oily oxime (8-Ia, 22 g, 84%). NMR (EM-390, CDCl$_3$, δ): 1.31 (3H, t, J=7,5 Hz, —COOCH$_2$CH$_3$), 4.34 (2H, q, J=7.5 Hz, —COOCH$_2$CH$_3$), 4.67 (2H, s, —CH$_2$OH), 5.80 (1H, brs, OH).

(2) Production of a hydroxy-protected compound (8-IIa).

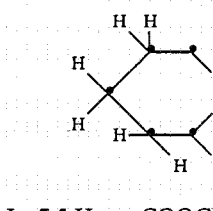

[8-IIa]

To a solution of the compound (8-Ia, 22 g, 0.126 moles) in anhydrous dichloromethane (370 ml) are added dihydropyrane (23 ml, 0.252 moles) and pyridinium p-toluenesulfonate (3.16 g, 0.0126 moles). The mixture is stirred at the same temperature for 1 hour. The reaction mixture is poured onto ice water and extracted with dichloromethane. The extract solution is washed with water, aqueous sodium hydrogen carbonate and saline, dried over magnesium sulfate and concentrated under reduced pressure to leave oily material (37 g). The oily material is purified by chromatography over silica gel (600 g) using a mixture of benzene and ethyl acetate (9:1) to give the compound (8-IIa, 13.8 g, 73%).

IR (film) 3230, 1739, 1705, 1630, 1302, 1210, 1135, 1022 cm$^{-1}$.

NMR (T-60, CDCl$_3$, δ): 1.33 (3H, t J=7.5 Hz, —COOCH$_2$CH$_3$), 1.51–1.98 (6H, m,

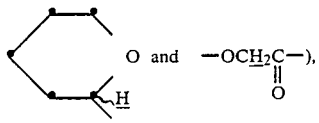

4.34 (2H, q, J=7.5 Hz, —COOCH$_2$CH$_3$), 4.74 (3H, brs,

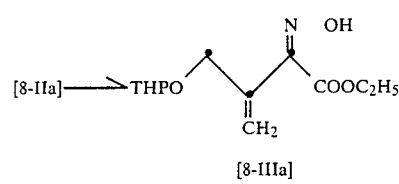

11.13 (1H, brs, =NOH).

(3) Production of the olefin (8-IIIa).

[8-IIa]⟶THPO... COOC$_2$H$_5$ / CH$_2$

[8-IIIa]

To a solution of the compound (8-IIa, 18.5 g, 71.4 millimoles) in anhydrous dichloromethane (95 ml) are added t-butyldimethylsilyl chloride (11.29 g, 74.9 millimoles) and triethylamine (11.0 ml, 78.5 millimoles), and the mixture is stirred at 3° C. for 1.5 hours and at room temperature for 30 minutes. The reaction mixture is poured into cold n-hexane. The separated triethylamine hydrochloride is removed by filtration and the filtrate is concentrated to afford the corresponding O-silyl compound (25.6 g).

IR (film): 1740, 1708, 1592, 1210, 1017, 994, 828 cm$^{-1}$.

NMR (CDCl₃, δ): 0.24 (6H, s), 0.93 (9H, s), 1.32 (3H, t, J=7.5 Hz), 1.45–1.93 (6H, m), 3.4–4.0 (2H, m), 4.35 (2H, q, J=7.5 Hz), 4.65 (1H, s), 4.71 (2H, brs).

To a suspension of methyltriphenylphosphonium bromide (79.02 g, 0.221 mole) in dry ether (790 ml) is added 1.67 N-butyllithium (128 ml, 0.214 moles) dropwise at room temperature under nitrogen. After stirring for 1 hour, the mixture forms yellow suspension. It is cooled to 5° C., mixed dropwise with the silyl compound obtained above (25.6 g) in ether (50 ml) at 4° to 5° C. over 30 minutes period, and then mixed at one time with hexamethyl-phosphorotriamide (37 ml, 0.214 moles). The mixture is stirred at 6° C. to 9° C. for 1 hour 20 minutes. To this mixture is added saturated ammonium chloride (200 ml) dropwise and solid material is removed by filtration. The filtrate is washed with water and saline, dried over magnesium sulfate, and concentrated under reduced pressure to leave oily material (36 g). The material is dissolved in tetrahydrofuran (260 ml), mixed with tetraethylammonium fluoride dihydrate (25.0 g, 135 millimoles), and stirred at 5° C. for 30 minutes and at room temperature for 1 hour. The reaction mixture is poured into ice water and extracted with ether. The extract solution is washed with water and saline, dried over magnesium sulfate and concentrated to remove the solvent affording oily material. It is purified by silica gel chromatography to afford the olefin compound (8-IIIa, 8.9 g 49%). mp. 71°–72° C.

IR (Nujol): 3180, 1729, 1608, 1230, 1027, 984 cm⁻¹.

NMR (EM-390, CDCl₃, δ): 1.36 (3H, t, J=7.5 Hz, —COOCH₂CH₃), 1.5–1.9 (6H, m,

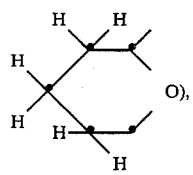

3.45–4.05 (2H, m,

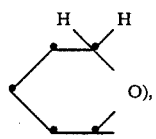

4.30 and 4.49 (2H, ABq, J$_{AB}$=15.0 Hz, THPOCH₂—), 4.39 (2H, q, J=7.5 Hz, —COOCH₂CH₃), 4.77 (1H, brs,

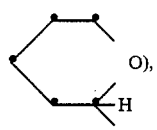

5.35 and 5.75 (each s, 2H, olefinic proton), 9.47 (1H, s, N—OH).

(4) Production of the hydroxy compound (8-IVa).

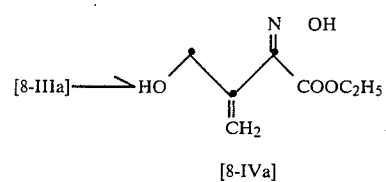

To a solution of the compound (8-IIIa, 1.028 g, 4.0 millimoles) in methanol (10 ml) is added p-toluenesulfonic acid hydrate (38 mg, 0.05 molar equivalents), and the mixture is stirred for 1 hour 45 minutes. The reaction mixture is concentrated to a fifth volume under reduced pressure and diluted with ethyl acetate. To this solution is added 1N-sodium hydroxide under ice cooling and the mixture is stirred for a while. The ethyl acetate layer is separated and washed with water and saline, dried over magnesium sulfate and concentrated under reduced pressure to remove the solvent. The residue is purified by chromatography over Lobar ® column B using a mixture of benzene and ethyl acetate (4:1 to 2:1) as eluting solvent to afford the compound (8-IVa, 0.69 g, quantitative). m.p. 38°–45° C.

IR (CHCl₃): 3570, 3270, 1740, 1630, 1092, 1032 cm⁻¹.

¹H-NMR (EM-390, CDCl₃, δ): 1.33 (3H, t, J=7.5 Hz, —COOCH₂CH₃), 4.36 (2H, brs, —CH₂OH), 4.37 (2H, q, J=7.5 Hz, —COOCH₂CH₃), 5.29 and 5.67 (each s, 2H, olefinic proton), 9.90 (1H, brs, =NOH).

¹³C-NMR (XL-100, CDCl₃, δ): 14.1 (—COOCH₂CH₃), 62.1 (—CH₂OH and —COOCH₂CH₃), 120.0 (>C=CH₂), 139.1 (>C=CH₂), 151.7 (>C=NOH), 163.8 (—COOC₂H₅).

(5) Production of an azetidinone compound (8-Va).

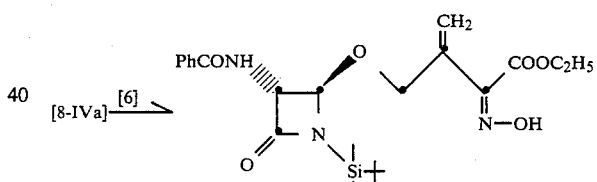

To a solution of silylated oxazorinoazetidinone compound (6, 540 mg, 1.78 millimoles) and the compound (8-IVa, 371 mg, 2.14 millimoles) in anhydrous ethyl acetate (1.1 ml) is added boron trifluoride etherate (11 ml, 0.05 molar equivalents), and the mixture is stirred at room temperature for 1 hour. The reaction mixture is diluted with ethyl acetate, washed with cold aqueous sodium hydrogen carbonate and saline, dried over magnesium sulfate and concentrated under reduced pressure to remove the solvent. The residue is purified by chromatography over Lobar ® column B using a mixture of benzene and ethyl acetate (4:1) to afford the compound (8-Va, 595 mg, 70%) and the compound (8-IVa, 149 mg).

The compound (8-Va): m.p. 72°–74° C.

IR (CHCl₃): 3560, 3260, 1755, 1740, 1663, 1602, 1580, 1083 cm⁻¹.

NMR (EM-390, CDCl₃, δ): 0.23 and 0.27 (each s, 6H, —Si(CH₃)₂—), 0.97 (9H, s, —SiC(CH₃)₃), 1.31 (3H, t, J=7.5 Hz, —COOCH₂CH₃), 4.29 and 4.46 (2H, ABq, J$_{AB}$=12 Hz, —OCH₂—), 4.34 (2H, q, J=7.5 Hz, —COOCH₂CH₃), 4.60 (1H, d, J=6.5 Hz,

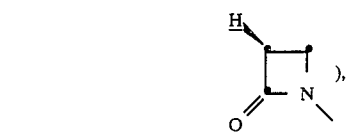

5.10 (1H, s,

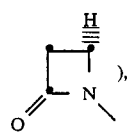

5.31 and 5.67 (each s, 2H, olefinic proton), 7.2–7.5 and 7.6–7.9 (each m, 6H, aromatic proton), 9.94 (1H, brs, N—OH).

(6) Production of the compound (8c).

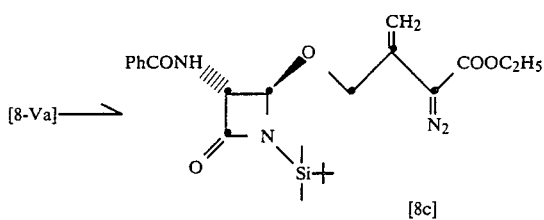

To a solution of the oxime (8-Va, 300 mg, 0.631 millimoles) in anhydrous dichloromethane (6 ml) cooled at −70° C. is added 1.67N-butyllithium (0.81 ml, 1.35 millimole) dropwise over 10 minutes period. The mixture is mixed with newly prepared O-mesytylenesulfonylhydroxylamine (285 mg, 1.35 millimoles) and stirred at −70° C. for 1 hour and at −50° C. to 0° C. for 2 hours. The reaction mixture is diluted with ice water, and extracted with dichloromethane. The extract solution is washed with water and saline, dried over magnesium sulfate and concentrated to remove the solvent affording oily material. This residual material is purified by chromatography over Lobar ® column B to give the diazoester compound (8c, 161 mg, 54%) and the compound (8-Va, 60 mg).

The compound (8c): IR(CHCl₃): 3425–3300, 2090, 1750, 1695, 1665, 1619, 1605, 1580, 1080 cm⁻¹.

NMR (EM-390, CDCl₃, δ): 0.22 and 0.29 (each s, 6H, —Si(CH₃)₂—), 0.97 (9H, s, —SiC(CH₃)₃), 1.26 (3H, t, J=7.5 Hz, —COOCH₂CH₃), 4.24 (2H, q, J=7.5 Hz, —COOCH₂CH₃). 4.44 (2H, brs, —OCH₂—), 4.68 (1H, d, J=6.3 Hz,

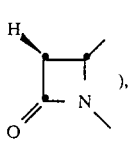

4.94 (1H, brs,

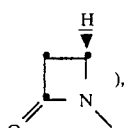

5.19 and 5.51 (each s, 2H, olefinic proton), 7.3–7.5 and 7.7–8.0 (each m, 6H, aromatic proton).

(7) Production of the compound (9c).

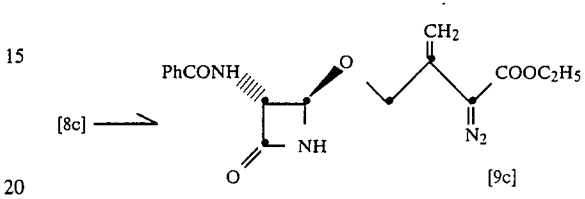

To a solution of the compound (8c, 109 mg, 0.231 millimoles) in tetrahydrofuran (0.6 ml) is added tetraethylammonium fluoride dihydrate (64 mg, 0.345 millimoles) under ice cooling (0° C. to 5° C.), and the mixture is stirred for 30 minutes at the same temperature. The reaction mixture is diluted with ice water and extracted with dichloromethane. The extract is washed with saline, dried over magnesium sulfate and evaporated under reduced pressure to remove the solvent affording oily substance. This substance is chromatographed over Lobar ® column B using a mixture of benzene and ethyl acetate (1:1) to give the compound (9c, 58 mg, 70%).

IR (CHCl₃): 3410, −3300, 2090, 1780, 1686–1666, 1617, 1580, 1094 cm⁻¹.

NMR (EM-390, CDCl₃, δ): 1.24 (3H, t, J=7.5 Hz, —COOCH₂CH₃), ~2.5 (1H, brs, $$-\overset{|}{\underset{}{N}}H),$$

4.21 (2H, q, J=7.5 Hz, —COOCH₂CH₃), 4.31 (2H, s, —OCH₂—), 4.78 (1H, d, J=7.0 Hz,

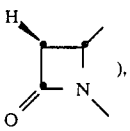

5.19 and 5.47 (each s, 3H, olefinic proton and

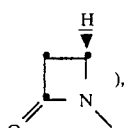

7.2–7.5 and 7.7–7.9 (each m, 6H, aromatic proton).

(8) Production of the objective compound (10c).

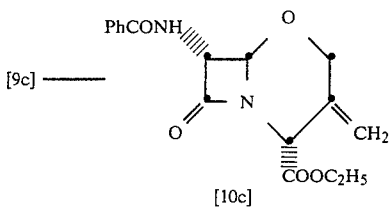

[9c] ———

[10c]

To a solution of the compound (9c, 55 mg, 0.153 millimoles) in anhydrous benzene (1.7 ml) is added dirhodium tetraacetate (1.3 mg, 2 molar percents), and the mixture is heated under reflux for 30 minutes. The reaction mixture is diluted with ethyl acetate, washed with saline, dried over magnesium sulfate and concentrated under reduced pressure to remove the solvent affording the crude compound (10c). This is purified by chromatography over Lobar ® column B using benzene and ethyl acetate (4:1) mixture as eluting solvent to give the compound (10c, 20 mg, 40%).

IR (CHCl$_3$): 3435, 1770, 1736, 1665 cm$^{-1}$.

$^1$H-NMR (EM-390, CDCl$_3$, δ): 1.25 (3H, t, J=7.5 Hz, —COOCH$_2$CH$_3$), 4.19 (2H, q, J=7.5 Hz, —COOCH$_2$CH$_3$), 5.01 (1H, d, J=7.8 Hz, C$_7$—H), 5.04 (1H, s, C$_4$—H), 5.24 and 5.28 (each s, 2H, olefinic proton), 5.31 (1H, s, C$_6$—H), 7.3–7.6 and 7.7–7.9 (each m, each 3H, aromatic proton).

$^{13}$C-NMR (XL-100A, CDCl$_3$, δ): 13.9 (—COOCH$_2$CH$_3$), 55.8 (C-4), 62.1 (C-2 and —COOCH$_2$CH$_3$), 83.9 (C-6), 117.2 (C-3'), 133.3 (C-3), 164.4 (C-8), 167.6 (—COOC$_2$H$_5$), 168.2 (—CONH$_2$ and aromatic carbon).

EXAMPLE 5

Production of 7α-benzamido-3-methylene-1-dethia-1-oxacepham-4α-carboxylic acid diphenylmethyl ester (10d).

(1) Production of the oxime (8-Ib)

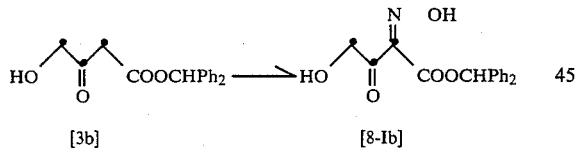

[3b]          [8-Ib]

To a solution of the compound (3b, 10 g, 35.2 millimoles) in acetic acid (10 ml) is added sodium nitrite (2.67 g, 38.7 millimoles) in water (10 ml) at 10° C. over 20 minutes period. The mixture is stirred at room temperature for 1 hour and then poured into ice water. The mixture is extracted with ethyl acetate. The extract is washed with saline, 1N-cold sodium hydroxide, water and saline, dried over magnesium sulfate and concentrated under reduced pressure to remove the solvent affording the crude oxime (8-Ib). The product is crystallized from a mixture of dichloromethane and n-hexane (1:5) to give pale yellow crystals (8.27 g, 75%). m.p. 116.3°–118° C. (decomp.).

IR (CHCl$_3$): 3430, 3150, 1740, 1690, 1601, 1220, 1041, 958, 698 cm$^{-1}$.

NMR (EM-390, CDCl$_3$:CD$_3$OD (9:1), δ): 3.37 (1H, brs, OH), 4.64 (2H, s, HOCH$_2$—), 7.07 (1H, s, —CHPh$_2$), 7.2–7.5 (10H, m, aromatic proton), 12.07 (1H, brs, =NOH).

(2) Production of the hydroxy-protected compound (8-IIb)

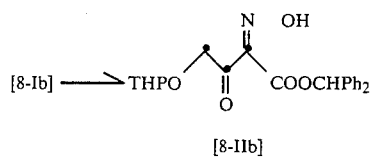

[8-IIb]

To a solution of the compound (8-Ib, 8 g, 25.5 millimoles) in anhydrous dichloromethane (15 ml) are added dihydropyran (6.44 g, 76.6 millimoles) and pyridinium p-toluenesulfonate (634 mg, 2.56 millimoles), and the mixture is stirred at room temperature for 1 hour. The reaction mixture is poured into ice water and extracted with dichloromethane. The extract solution is washed with water, aqueous sodium hydrogen carbonate and saline, dried over magnesium sulfate and concentrated under reduced pressure to remove the solvent affording oily material. This is purified by chromatography over silica gel (150 g) using a mixture of benzene and ethyl acetate (4:1) as eluting solvent to give the compound (8-IIb, 8.02 g, 79%). A part of the compound is recrystallized from a mixture of ether and n-hexane to obtain crystals melting at 128° to 129° C. (decomp.).

IR (Nujol): 3180, 1747, 1703, 1626, 1198, 1141, 1026, 694 cm$^{-1}$.

NMR (EM-390, CDCl$_3$, δ): 1.3–1.9 (6H, m,

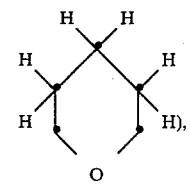

), 3.3–4.1 (2H,

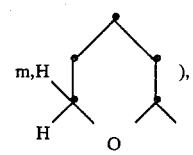

m, H ), 4.78 (2H, s, —OCH$_2$—), 7.07 (1H, s, CHPh$_2$), 7.2–7.5 (10H, m, aromatic proton), 10.23 (1H, brs, =NOH).

(3) Production of the hydroxy compound (8-IVb)

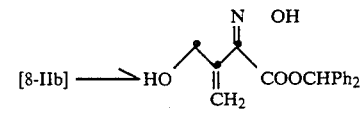

[8-IVb]

To a solution of the compound (8-IIb) 7.3 g, 18.4 millimoles) in dry dichloromethane (73 ml) are added triethylamine (3.3 ml, 23.9 millimoles) and t-butyldimethylsilyl chloride (2.91 g, 19.3 millimoles) dropwise under ice cooling (0° to 3° C.), and the mixture is stirred at 3° C. to room temperature for 2 hours. The reaction mixture is poured into a mixture of ether and n-hexane (1:1). Separated triethylamine hydrochloride is removed by filtration and the filtrate is dried and concentrated under reduced pressure to give silylated compound.

To a suspension of methyl-triphenylphosphinium bromide (20.4 g, 57.04 millimoles) in dry ether (200 ml) is added 1.6N-butyllithium solution (34.5 ml, 55.2 millimoles at room temperature, and the mixture is stirred for 45 minutes. This yellow suspension is cooled at 4° C. and a solution of above stated silylated compound in ether (70 ml) is added dropwise thereto at 4° C. to 6° C. Then the mixture is diluted with hexamethylphosphorotriamide (9.6 ml, 55.2 millimoles) and stirred at 4° C. to 6° C. for 1 hour. The reaction mixture is diluted with saturated ammonium chloride and extracted with ethyl acetate. The extract solution is washed with water and saline, dried over magnesium sulfate and concentrated under reduced pressure to leave an oily material. The material is purified by chromatography over Lobar ® column B using a mixture of benzene and ethyl acetate (9:1) as eluting solvent to afford the silylated olefin compound (8-III'b) 6.09 g, 65%).

IR (CHCl$_3$): 1732, 1620, 1596 cm$^{-1}$.

NMR (CDCl$_3$, δ): 0.14 (6H, s, —Si(CH$_3$)$_2$—), 0.85 (9H, s, —SiC(CH$_3$)$_3$), 1.2–1.8 (6H, m,

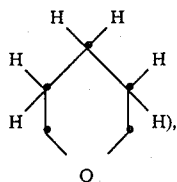

3.3–4.0 (2H,

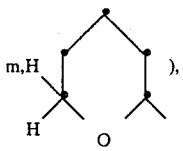

4.24 and 4.50 (2H, ABq, J=15 Hz, —CH$_2$OTHP), 4.66 (1H, brs,

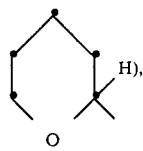

5.16 and 5.68 (each s, 2H, olefinic proton), 7.09 (1H, s, —CHPh$_2$), 7.1–7.6 (10H, m, aromatic proton).

To a solution of the compound (8-III'b, 6.09 g, 11.9 millimoles) in 1N-hydrogen chloride in methanol (350 ml), and the mixture is stirred at 0° C. for 12 hours. The reaction mixture is concentrated under reduced pressure to about a third volume, poured into saturated saline and extracted with ethyl acetate. The extract solution is washed with aqueous sodium hydrogen carbonate, water and saline, dried over magnesium sulfate and concentrated under reduced pressure to remove the solvent. The residue is crystallized from a mixture of dichloromethane and n-hexane to afford the compound (8-IVb, 85%, 3.16 g). m.p. 110°–111° C.

IR (Nujol): 3400, 3230, 3170, 1715, 1624, 1612, 1584, 1237, 995, 690 cm$^{-1}$.

$^1$H-NMR (EM-390, CDCl$_3$, δ): 2.98 (1H, brs, —CH$_2$OH), 4.29 (2H, brs, —CH$_2$OH), 5.03 and 5.48 (each s, 2H, olefinic proton), 7.10 (1H, s, —CHPh$_2$), ~7.3 (10H, brs, aromatic proton), 9.38 (1H, brs, =NOH).

$^{13}$C-NMR (XL-100A, CDCl$_3$, δ): 62.7 (—CH$_2$OH), 78.6 (—COOCHPh$_2$), 120.7 (>C=CH$_2$), 138.9 (>C=CH$_2$), 151.7 (>C=NOH), 162.4 (—COOCHPh$_2$), 127.5, 128.3, 128.5 and 139.1 (aromatic carbon).

(4) Production of the azetidinone compound (8-Vb)

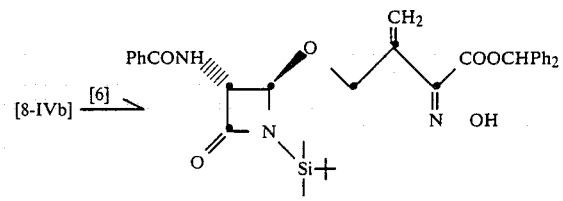

To a solution of the oxazoline compound (6,303 mg, 1.0 millimoles) and the compound (8-IVb, 327 mg, 1.05 millimoles) in anhydrous ethyl acetate (0.6 ml) is added boron trifluoride etherate (6.3 μl, 0.05 millimoles), and the mixture is stirred under nitrogen for 50 minutes at room temperature. The reaction mixture is diluted with ethyl acetate, washed with cold sodium hydrogen carbonate solution, water and saline, dried over magnesium sulfate and concentrated under reduced pressure to remove the solvent affording oily material. The material is purified by chromatography over Lobar ® column B using a mixture of benzene and ethyl acetate (4:1) and crystallizing from a mixture of ether and petroleum ether to give the compound (8-Vb, 417 mg, 74%). (The compound (8-IVb, 96 mg) is also recovered.) m.p. 146°–7° C.

IR (Nujol): ~3200, 1740, 1635, 1225, 1080 cm$^{-1}$.

NMR (EM-390, d$_6$-acetone, δ): 0.25 and 0.28 (each s, 6H, —Si(CH$_3$)$_3$), 0.99 (9H, s, —SiC(CH$_3$)$_3$—), 4.42 and 4.47 (2H, ABq, J=13.5 Hz, —OCH$_2$—), 4.81 (1H, d, J=7.5 Hz,

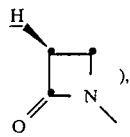

5.26 and 5.65 (each s, 2H, olefinic proton), 5.12 (1H, s,

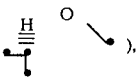

7.11 (1H, s, —CHPh$_2$), 7.2–7.6 and 7.8–8.0 (each m, 15H, aromatic proton), 8.45 (1H, d, J=7.5 Hz, —CONH—).

(5) Production of the compound (8d)

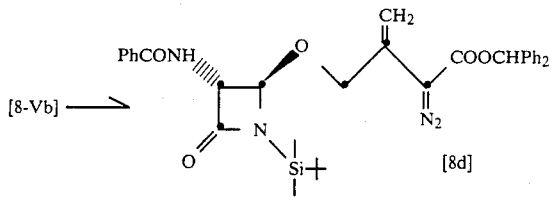

[8-Vb] ⟶ [8d]

To a solution of the compound (8-Vb, 390 mg, 0.635 millimoles) in dry dichloromethane (8 ml) cooled at −65° C. is added 1.67N-butyllithium (820 μl, 1.37 millimoles) under nitrogen over 5 minutes period. To this mixture is added O-mesitylenesulfonylhydroxylamine (287 mg, 1.34 millimoles) at −70° C. over 20 minutes. The mixture is stirred at the same temperature for 1 hour, −40° C. to −35° C. for 1 hour, −30° C. to 0° C. for 2 hours. The reaction mixture is poured into ice water, and extracted with ethyl acetate. The extract is washed with water and saline, dried over magnesium sulfate and concentrated under reduced pressure. The residue is purified by chromatography over Lobar ® column B using a mixture of benzene and ethyl acetate (9:1 to 4:1) affording the compound (8d) as pale yellow foam (198 mg, 51%). (The starting compound (8-Vb, 52 mg, 13%) is also recovered.)

IR (CHCl₃): 3430–3310, 2098, 1754, 1702, 1670, 1618, 1602, 1582, 1080 cm⁻¹.

NMR (EM-390, CDCl₃, δ): 0.15 and 0.23 (each s, 6H, —Si(CH₃)₂), 0.93 (9H, s, —SiC(CH₃)₃), 4.47 (2H, s, —OCH₂—), 4.54 (1H, d, J=6.5 Hz,

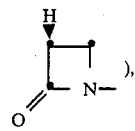

4.87 (1H, s, 5.21 and 5.57 (each s, 2H, olefinic proton), 6.99 (1H, s, —CHPh₂), 7.2–7.5 and 7.7–7.9 (each m, 15H, aromatic proton).

(6) Production of the compound (9d)

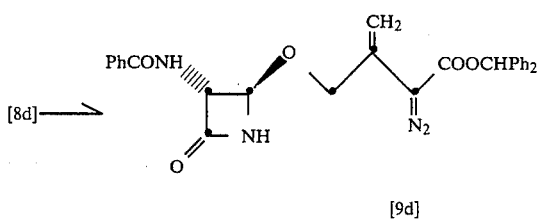

[8d] ⟶ [9d]

To a solution of the compound (8d, 160 mg, 0.262 millimoles) in dry tetrahydrofuran (1.6 ml) is added tetraethylammonium fluoride dihydrate (58 mg, 0.314 millimoles) under ice cooling, and the mixture is stirred at the same temperature for 55 minutes. The reaction mixture is poured into saturated saline and extracted with dichloromethane. The extract is washed with water and saline, dried over magnesium sulfate and concentrated to remove the solvent. The residual oily substance is purified by chromatography over Lobar ® column B using a mixture of benzene and ethyl acetate (2:1) affording the compound (9d, 96 mg, 74%).

IR (CHCl₃): 3410, 2085, 1781, 1692, 1670, 1615, 1601, 1580, 1070 cm⁻¹.

NMR (EM-390, CDCl₃, δ): 2.17 (1H, brs,

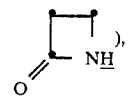

4.25 (2H, brs, —CH₂O—), 4.70 (1H, d, J=6.5 Hz,

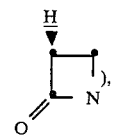

5.12 (2H, brs,

and olefinic proton), 6.93 (1H, s, —CHPh₂), 7.1–7.9 (16H, m, —CONH— and aromatic proton).

(7) Production of the objective compound (10d)

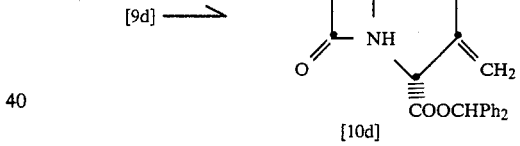

[9d] ⟶ [10d]

To a solution of the compound (9d, 84 mg, 0.169 millimoles) in dry benzene (1.7 ml) is added dirhodium tetraacetate (1.3 mg, 1.7 molar percent), and the mixture is refluxed for 15 minutes whereby nitrogen ceased to evolve and the reaction completes. The reaction mixture is freed from the solvent and chromatographed over Lobar ® column B using a mixture of benzene and ethyl acetate (2:1) as eluting solvent. The eluate is recrystallized from ether to give the compound (10d, 34 mg, 43%). m.p. 155°–156° C.

IR (CHCl₃): 3440, 3330, 1775, 1742, 1670, 1602, 1584, 1170, 1065, 908 cm⁻¹.

¹H-NMR (EM-390, CDCl₃, δ): 4.19 (2H, brs, C₂—2H), 4.99 (1H, d, J=7.5 Hz, C₇β—H), 5.14 (1H, s, C₄β—H), 5.25, 5.28 and 5.31 (each s, 3H, C₆α—H and olefinic proton), 6.84 (1H, s, —CHPh₂), 7.2–7.5 and 7.7–7.9 (each m, 16H, —CONH— and aromatic proton).

¹³C-NMR (XL-100A, CDCl₃, δ): 56.0 (C-4), 64.3 (C-7), 67.8 (C-2), 78.8 (—CHPh₂), 84.0 (C-6), 117.6 (C-3'), 132.9 (C-3), 163.4 (—COOCHPh₂), 167.1 (C-8), 167.4 (—CONH— and aromatic carbon).

What we claim is:

1. A 4-oxygenated butyric acid derivative of the formula $Y^1CH_2CR^2COOR$ with $X$ double-bonded wherein R is carboxy protecting group;

$R^2$ is (1) methylene, (2) hydroxyiminomethylene, (3) hydroxyiminomethylene protected by tri-$C_1$ to $C_5$-alkylsilyl, 1-$C_1$ to $C_5$-alkoxy-$C_1$ to $C_5$-alkyl, tetrahydrofuranyl or tetrahydropyranyl, or (4) diazomethylene;

X is methylene; and $Y^1$ is a group of the formula

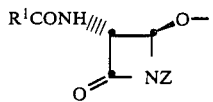

in which $R^1$ is (1) $C_1$ to $C_{10}$-alkyl which is unsubstituted or substituted by phenoxy (2) benzyl, (3) phenyl, (4) methylphenyl, (5) dimethylphenyl, (6) cyanophenyl, (7) nitrophenyl, (8) methoxyphenyl or (9) chlorophenyl and Z is hydrogen or a N-protecting group from the group of $C_1$ to $C_5$-alkanoyl and tri-$C_1$ to $C_5$-alkylsilyl.

2. A compound as claimed in claim 1 wherein $R^2$ is hydroxyiminomethylene or hydroxyiminomethylene protected as defined in claim 1.

3. A compound as claimed in claim 1 wherein the N-protecting group Z or the protecting group for hydroxyiminomethylene $R^2$ is tri-$C_{1-5}$alkylsilyl.

* * * * *